United States Patent [19]
Finneran

[11] Patent Number: 6,002,957
[45] Date of Patent: Dec. 14, 1999

[54] EMG ELECTRODE ARRAY SUPPORT BELT

[75] Inventor: Mark T. Finneran, Wooster, Ohio

[73] Assignee: Paraspinal Diagnostic Corporation, Wooster, Ohio

[21] Appl. No.: 09/059,783

[22] Filed: Apr. 14, 1998

Related U.S. Application Data

[60] Provisional application No. 60/043,092, Apr. 15, 1997.

[51] Int. Cl.⁶ ................................................. A61B 5/0492
[52] U.S. Cl. ........................ 600/382; 600/390; 600/393; 600/546
[58] Field of Search ........................... 600/372, 382–384, 600/388–390, 393, 394, 546; 607/148, 149, 152

[56] References Cited

U.S. PATENT DOCUMENTS

| | | |
|---|---|---|
| 3,525,330 | 8/1970 | Greene . |
| 3,612,061 | 10/1971 | Collins et al. ........................... 607/148 |
| 3,641,993 | 2/1972 | Gaarder et al. . |
| 4,026,300 | 5/1977 | De Luca et al. . |
| 4,031,882 | 6/1977 | De Luca . |
| 4,033,333 | 7/1977 | DeSalvo et al. ........................ 600/393 |
| 4,046,141 | 9/1977 | De Luca . |
| 4,381,012 | 4/1983 | Russek . |
| 4,387,723 | 6/1983 | Atlee, III et al. . |
| 4,570,225 | 2/1986 | Lundy . |
| 4,572,197 | 2/1986 | Moore . |
| 4,611,284 | 9/1986 | Mc Gill . |
| 4,667,513 | 5/1987 | Konno . |
| 4,709,704 | 12/1987 | Lukasziewicz . |
| 4,751,928 | 6/1988 | Hallon et al. ........................... 600/393 |
| 4,967,038 | 10/1990 | Gevins et al. .......................... 600/393 |
| 5,085,225 | 2/1992 | De Luca . |
| 5,085,226 | 2/1992 | De Luca . |
| 5,163,440 | 11/1992 | De Luca . |
| 5,224,479 | 7/1993 | Sekine ..................................... 600/389 |
| 5,462,065 | 10/1995 | Cusimano . |
| 5,483,970 | 1/1996 | Rosenberg . |
| 5,645,073 | 7/1997 | Kadefors . |
| 5,662,118 | 9/1997 | Skubick . |
| 5,704,368 | 1/1998 | Asano . |

*Primary Examiner*—Lee Cohen
*Attorney, Agent, or Firm*—Ralph E. Jocke; Christopher L. Parmelee

[57] ABSTRACT

An electrode array for collecting surface electromyographic (EMG) signals from a patient consists of 63 electrically conductive electrodes supported in a non-conductive, flexible pad in a predetermined pattern of nine rows and seven columns of equally spaced electrodes. The flexible pad allows the electrode array to conform to the external curvature of the patient, while the 9×7 rectangular array of electrodes provides a unique pattern related to the configuration of underlying muscle groups of the patient. This allows the sensor pad to be uniquely positioned relative to the patient's anatomy and to provide signals representative of the muscle activity, which can then be electronically displayed in a corresponding pattern, for evaluation by the attending physician.

17 Claims, 21 Drawing Sheets

Signal Processing Subsystem (102)

EMG ELECTRODE ARRAY SUPPORT BELT

This application claims benefit of Provisional Application Serial No. 60/043,092 filed Apr. 15, 1997.

TECHNICAL FIELD

This invention relates to a method and apparatus for monitoring and displaying the condition of muscles in a muscle group by the sensing and analysis of electromyographic signals derived from a non-invasive body surface electrode array positioned close to the muscle group.

BACKGROUND ART

Knowledge of the presence of electromyographic (EMG) signals in the muscles of humans, and the change of these signals with muscle activity, spawned development of electronic devices and techniques; for monitoring those signals for the evaluation of the muscles. Human musculature, however, involves many hundreds of muscles in various muscle groups, which interact to provide skeletal support and movement. Much of the recent development has been concerned with the techniques and/or devices for monitoring the signals, analyzing the information obtained and providing reliable and useful data for the patient or treating physician. Recent developments in computer technology have also provided an assist in this regard. With higher speeds of operation and greater computing capacity, the capability for handling and operating upon a multiplicity of signals in a reasonable evaluation period has become feasible. However, because of the complexity of the muscle structure and the difficulty in obtaining useful, reliable signals, preferably in a non-invasive mode, obtaining a useful definition of the muscle activity in a reasonable amount of time and in an economical manner is still subject to current development.

Typical of this prior art is the device described by D. Prutchi in the publication "A High-Resolution Large Array (HRLA) EMG System", published September 1995 in Med. Eng. Phys., Vol. 17, 442–454. Prutchi describes a bracelet which may be wrapped about a body limb and which contains 256 surface electrodes to record the electrical activity of underlying muscles. The electrodes are arranged in eight groups of thirty-two electrode linear arrays directly connected to buffer boards in close proximity of the electrodes. Further processing of the electrical signals is performed to provide a desired signal analysis, in this instance primarily being concerned with the bidirectional propagation of a compound potential in a single muscle in the upper arm of a human subject or a histogram of total power contribution from active fibers in a subject muscle, both being presented in charted format.

U.S. Pat. No. 5,086,779 to DeLuca, et al., describes a back analysis system of plural electrodes coupled to a computer system for processing the signals and to provide graphical representations of results. DeLuca's invention relates primarily to isolating particular muscle groups by the use of support and restraint devices which limit the movement of the patient's torso in predetermined patterns correlated to the desired muscle groups. DeLuca's electrode array consists of separate electrodes individually placed at desired locations on a patient's back.

U.S. Pat. No. 5,058,602 to Brody describes a method of electromyographic scanning of paravertebral muscles comprising measuring electrical potentials bilaterally across segments of the spine. Readings are categorized into different patterns which are indicative of different muscular conditions. Brody suggests equipment useful within his described techniques as an available EMG scanner having electrodes spaced 2.5 cm apart and a computer component, but provides few details on the equipment or an indication of usefulness for isolating certain muscles or muscle groups.

U.S. Pat. No. 5,318,039 to Kadefors, et al., describes a method and apparatus for detecting electromyographic signals, processing them and providing an indication of the change of the signal from a predetermined norm. Kadefors' electrode system comprises three electrodes, one of which is a reference marker. This electronic apparatus, in essence, includes a sample and hold function in which current responses can be compared to earlier responses and an indication provided based on the differences detected.

U.S. Pat. No. 5,505,208 to Toormin, et al., describes a method for determining the status of back muscles wherein EMG signals are monitored from a number of electrodes placed in a pattern on a patient's back, the activity of each electrode is determined and the results stored. A database of results provides a standard from which comparisons can be made to determine deviations or abnormalities, as a device for the care and management of the patient's dysfunction.

U.S. Pat. No. 5,513,651 to Cusimano, et al., describes a portable electronic instrument for monitoring muscle activity, using standard ECG electrodes and a computer for analyzing the detected signals. The electrodes are applied individually at predetermined locations and a range of motion device is employed to generate signals related to a particular muscle group. Output plots are produced to provide an indication of results, apparently in the form of printouts of information reflecting any deviations from the norm of expected muscle activity.

While the prior art devices describe much sophistication in the detection and analysis of EMG signals, there is a need for equipment which is capable of being utilized by the average skilled examining physician who, for example, uses and is familiar with the techniques of physical examination and palpation of the paraspinous musculature of the thoracolumbosacral spine.

DISCLOSURE OF INVENTION

An object of the present invention is to provide improved surface EMG equipment, readily useable by the skilled examining physician, for the diagnosis or treatment monitoring of patients with low back pain.

A further object of the present invention is to provide an improved clinical tool which is portable and which uses non-invasive techniques for the collection of signals.

A further object of the present invention is to provide improved EMG equipment which provides a visual display of the activity of muscles or muscle groups.

A further object of the present invention is to provide improved EMG equipment in which the visual display of muscle activity is juxtaposed over a visual display of normal muscle anatomy for correlation by the examining physician.

A further object of the present invention is to provide improved EMG equipment in which the visual display can be selected for specific musculature identified by the examining physician.

A further object of the present invention is to provide improved EMG equipment which utilizes a single detector pad of electrodes in which the electrodes are arranged in a specific array, to monitor instantaneously all specific muscles in a muscle group of a patient.

Further objects of the present invention will be made apparent in the following Best Modes for Carrying Out the Invention and the appended Claims.

The electromyographic (EMG) diagnostic system of the present invention is particularly suited for evaluation of the lower back of a human and consists essentially of a sensor pad for collecting and conditioning EMG signals, electronic equipment including a computer for signal discrimination and evaluation and a display device for providing a visual display of the activity of selected musculature. A ground electrode is positioned on the patient. The electronic equipment serves to receive signals from the sensor pad which is pressed against the lower back of a patient in a predetermined location and held immobile relative to the patient such as by strap with foam backing, an inflatable bladder, an adhesive pad or other convenient arrangement. Signals from individual electrodes are conditioned by the electrical equipment, discriminated from noise signals and the like and evaluated relative to the signal received from the reference electrode. Computer apparatus is then used to analyze the signals, and can combine the signals in various patterns to provide an analysis of the muscular anatomy of the lower back and the activity of such muscles.

A preferred technique for signal monitoring is to determine the RMS voltage of the sensed signals over a predetermined time interval. The RMS voltage is converted to a visual display representative of the power level, which display then provides a visual indication of those locations where a higher level of muscle activity is detected. The RMS signal technique is advantageous in providing a device for averaging the highly sensitive and often variable individual electrode signals which are susceptible to changes in contact resistance at the electrode, the human skin resistance, stray field fluctuation, inadvertent movements by the patient, and the like, which can introduce false signals, and mask the desired muscle activity signals.

A visual display of the sensed muscle activity is provided on a monitor, such as a cathode ray tube type monitor, which may then be evaluated by the attending physician. A predetermined display of normal back anatomy is displayed simultaneously on the monitor to assist the physician in his evaluation. For example colorization of the resultant sensed display with different colors representing the degree of contraction thus provides a vivid indication of abnormal activity of the muscle. Normal back anatomy is provided in this invention by the selection from an inventory of various back muscle configurations which depict different layers of back muscles of the normal human patient. These configurations are selectable by the physician for comparison with the sensed muscle activity pattern in order to assist in providing a correlation between the two. Further control is provided in that the physician not only can alter the physical configuration of the sensed signal display but also can adjust the intensity or colorization of the sensed display to render a more pronounced image of abnormal muscle activity relative to normal back anatomy. Visual display modification is achieved by adjustment of the sensitivity of the sensed signal detector or by increasing the level of signal over which a visual indication is provided.

BRIEF DESCRIPTION OF DRAWINGS

FIG. 28 is a chart of a portion of the software program of the invention, showing a header format.

FIG. 29 is a chart of a portion of the software program of the invention, showing a listing of files developed therein.

FIG. 30 is a chart of a portion of the software program of the invention, showing generally the Source File Structure.

BEST MODES FOR CARRYING OUT INVENTION

Figure 1:
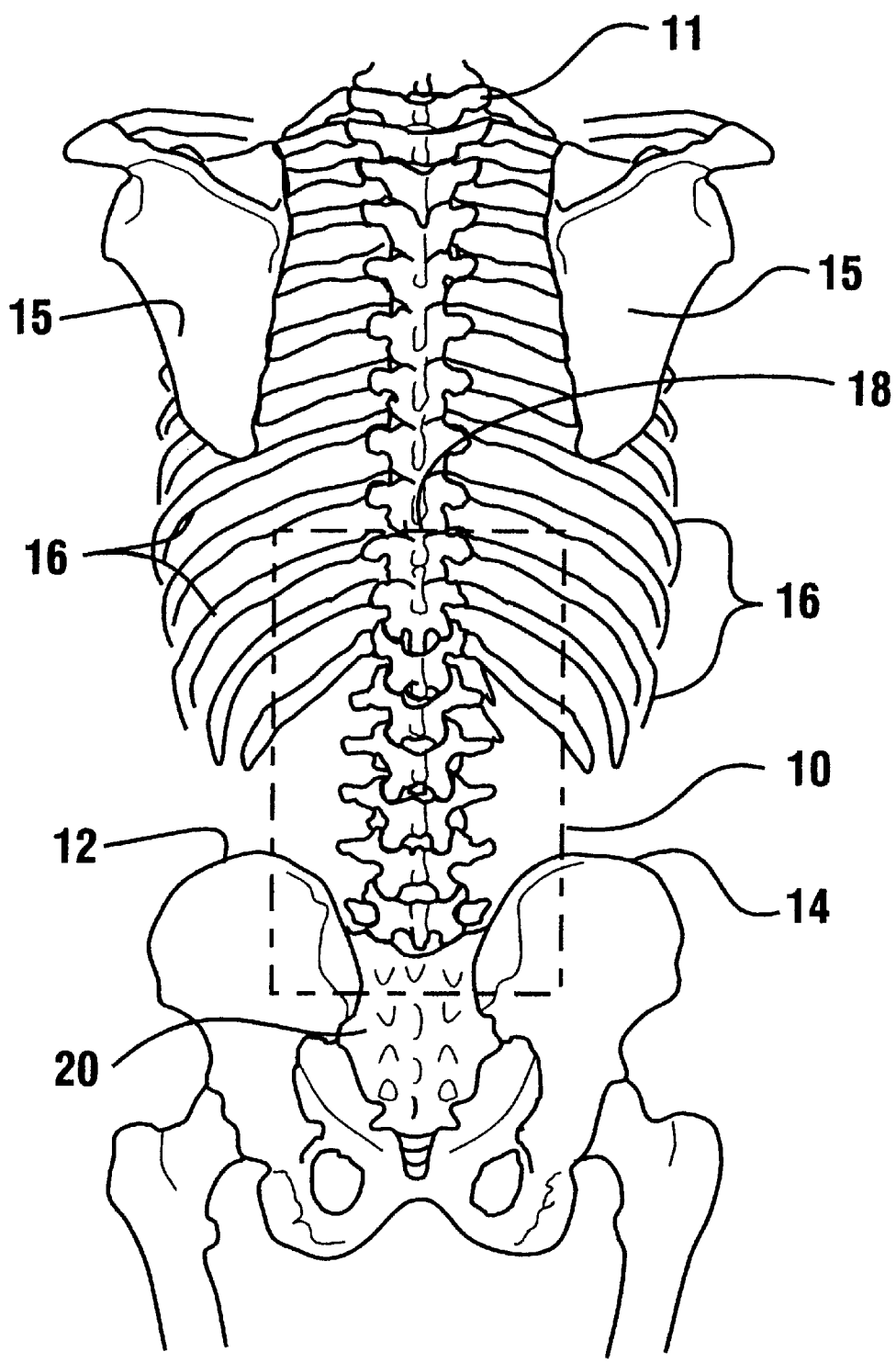
FIG. 1 is a simplified schematic overview of a portion of the lower back skeletal structure of a patient with an outline of the sensor pad portion of the invention depicted in position thereover.

Referring now to the drawings, and initially to FIG. 1, there is shown in schematic form the sensor pad 10 of the intention positioned in relation to a partial skeletal showing of the lower back of a patient, the latter comprising a spine 11, left posterior superior iliac crest 12, right posterior superior iliac crest 14, portions of the scapula 15 and ribs 16. As will be described in greater detail hereafter, sensor pad 10 is a device for collecting electromyographic (EMG) signals from the underlying muscle structure supporting and providing movement to the spine 11. The muscle structure is a complicated array of muscles consisting of at least sixty-nine erector and intrinsic muscles in the thoracolumbosacral spine extending from about the tenth thoracic vertebrae 18 to the sacrum 20. These are the primary muscles with which this invention is concerned and occur in layers from deep to superficial. Also formed in the superficial region of the lower back are several muscles which are not classical erector muscles, which while important, are not the principal interest of this invention. These latter muscles may also produce EMG signals which serve to complicate the evaluation process and may require discrimination, but which are not a primary source of the lower back pain syndrome affecting the greater portion of the patient population.

EMG signals and their relation to muscle functions are well understood at the current state of investigations. Muscles are controlled by nerves, the latter transmitting an electrical signal to a particular muscle and causing contraction thereof. The muscle itself is a volume conductor reacting to the signal of the associated nerve. There is a voltage change that occurs when a muscle contracts creating an electric potential that is directly proportional to the strength of contraction and that can be captured from the external surface area of the patient, in this instance being the surface area of the thoracolumbosacral spine. Currently, there is technology which allows certain evaluations of the electrical activity of muscles such as EMGs or EKGs and which may be displayed in analog, waveform or spectral forms. Available technology and the associated devices however are deficient in not being able to select all muscles in a muscle region in a manner which is conducive to evaluation by an attending physician.

Figure 2:
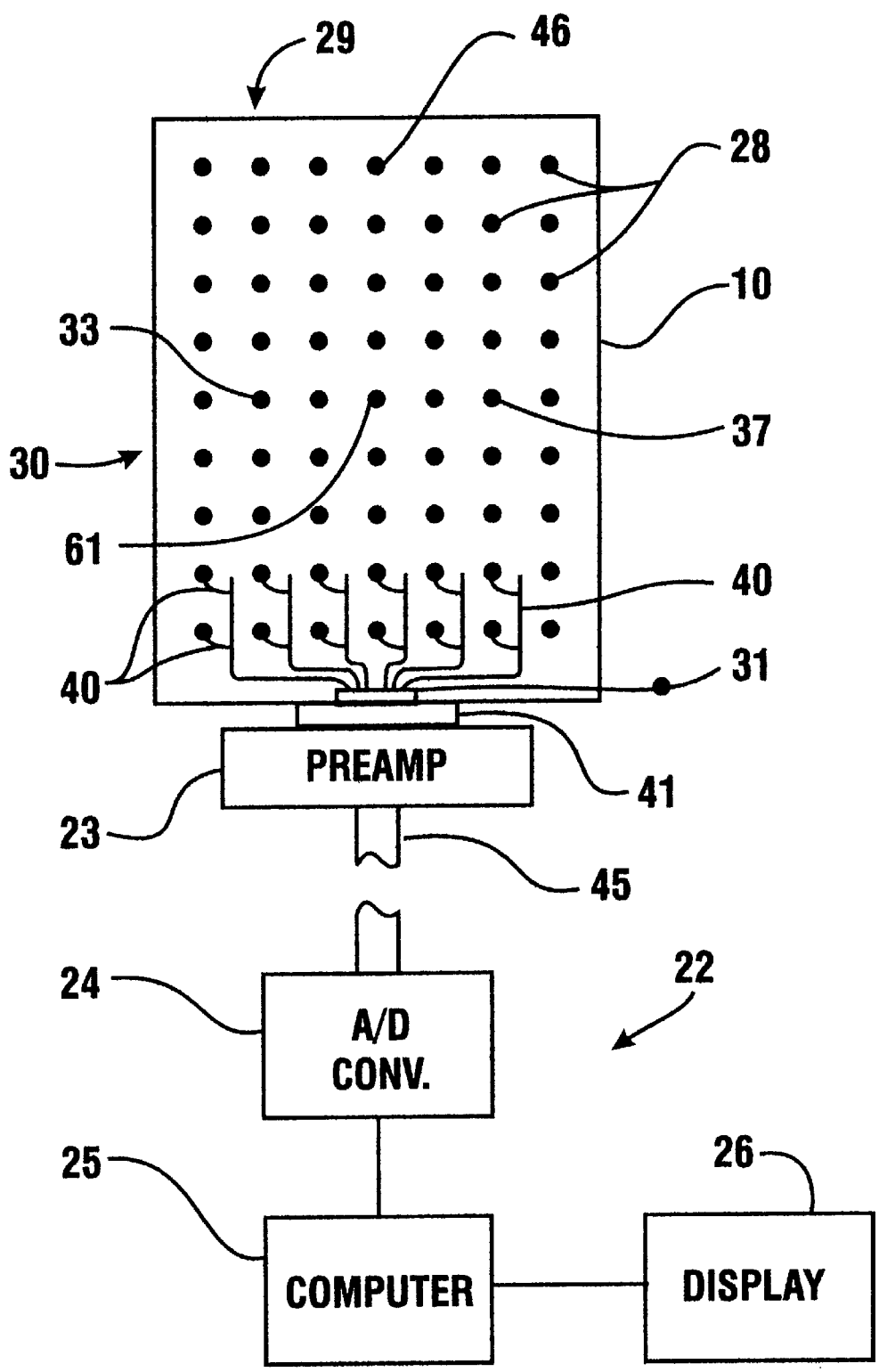
FIG. 2 is a schematic view of the apparatus of the invention, comprising the sensor pad in connection with electronic apparatus including a computer and display unit.

Referring now to FIG. 2 there is shown in schematic form, the essential elements of this invention as comprising sensor pad 10 and electronic apparatus 22 comprising preamplifier 23, converter 24, computer 25 and display unit 26. Sensor pad 10 is a flat rectangular piece of siliconized rubber, approximately 0.062 inch thick, measuring about 12×12 inches and with a Durometer hardness on the order of 20 to 40. One source for sensor pad 10 is Fairprene Industrial Products, Inc. of Fairfield, Conn.

Sensor pad 10 further comprises an array of sixty-three electrodes 28, preferably made of 316 L stainless steel. Electrodes 28 are arranged in a 7×9 pattern, with the electrodes in each row and column being spaced 1.162 inches apart on center. A central column 29 of nine electrodes 28 is located in the middle of sensor pad 10 to overlay the spine 11 of the patient, and three equally spaced parallel columns of nine electrodes each are positioned on either side of the central column 29. Similarly, a central row 30 of seven electrodes 28 is positioned near the center of sensor pad 10, and four parallel rows of seven electrodes each are positioned on either side of central row 30. Ground electrode 31, is a standard electrode preferably positioned on a wrist of the patient.

Figures 4, 5, 6:
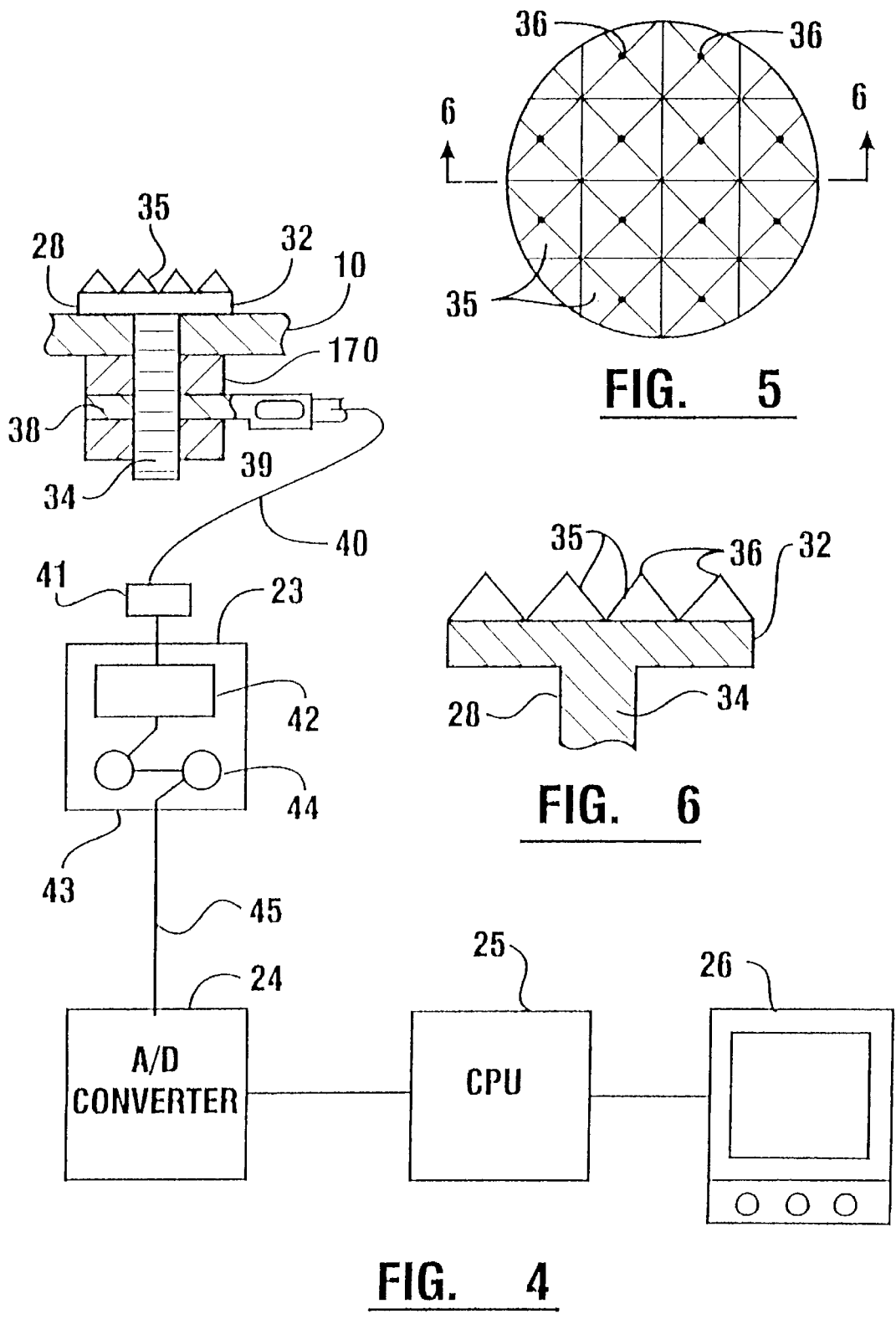
FIG. 4 is a view partly in cross-section of a portion of the sensor pad of the invention, showing a single electrode and the electrical connection to the computer portion of the invention.
FIG. 5 is an enlarged plan view only of the single electrode shown in FIG. 4.
FIG. 6 is a cross-sectional view of a single electrode taken along the lines 6—6 of FIG. 5.

All of the electrodes 28, are identical and one configuration is shown in greater detail in FIGS. 4–6 as comprising a pyramidal tipped, bolt-shaped structure having a head 32 and integral threaded shaft 34. Head 32 is circular and includes a plurality of pyramids 35 distributed substantially evenly and projecting outwardly of the upper surface of head 32 to form the patient-contacting surface of electrode 28. Head 32 is preferably 0.375 inches in diameter and has a thickness of 0.08 inches from the lower surface thereof at the junction with shaft 34, to the tips 36 of pyramids 35. Pyramids 35 are formed by grinding electrode head 32 in a series of parallel and orthogonal passes or by electromachining to produce a square pyramidal shape having an altitude of 0.042 inches, an angle of 90 degrees between opposing pyramid faces and culminating in a tip 36 having a radius of 0.005 inch. Tips 36 are spaced 0.094 inches from one another and in this embodiment of the invention, result in an electrode 28 having twelve pyramids 35 and tips 36 at the signal-collecting surface thereof. It has been determined that this configuration of electrode 28 is particularly useful in enhancing lower contact resistance when placed in position on a patient, thereby assuring better EMG signal reception and greater accuracy of the measurement.

Each electrode 28 is mounted in an aperture in sensor pad 10 and retained in position by a nut 170 threaded to shaft 34.

Alternatively, electrode 28 may have an unthreaded shaft 34 and be retained in position by a push connector. A solderless ring connector 38 is also received on shaft 34 and is firmly secured by outer nut 39 to provide an electrical interconnection with the signal gathering surface of electrode 28. An electrode wire 40 is crimped to connector 38 and each of the electrode wires 40 is routed over the surface of sensor pad 10 to a pigtail at the upper end of sensor pad 10 which terminates at a connector 41. Each electrode wire 40 is preferably a 30 gauge, multi strand, flexible copper wire which allows for some deformation of sensor pad 10 to conform to the lower back of a patient, while connector 41 allows for releasable connection of the sensor pad to the electrical circuitry to facilitate substitution of components of the apparatus of the invention. With an electrode head 32 diameter and spacing, as mentioned in the preferred embodiment, the edge to edge spacing of electrodes 28 in each column 29 and row 30 is 2.0 centimeters or approximately 0.79 inches. This has been determined to provide enough distance between electrodes 28 to result in a meaningful signal difference between electrodes.

The electronic circuitry comprising preamplifier 23 is located near sensor pad 10 for conditioning and amplifying the signals received at electrodes 28. Electrode wire 40 is connected to buffer amplifier 42, and the signal in turn is routed to low pass filter 43 and high pass filter 44 for each electrode 28 of sensor pad 10. Conditioning of the signals preferably occurs closely adjacent the patient and avoids remote transmission of very low level signals in a background of randomly generated noise signals. Buffer amplifier 42 minimizes leakage current through the electrode and errors due to electrode impedance changes. High pass filter 44 serves as an anti-aliasing filter, and low pass filter 43 prevents saturation of analog to digital (A/D) converter 24 by offset voltages, such filters being well understood in the art.

Figure 24:
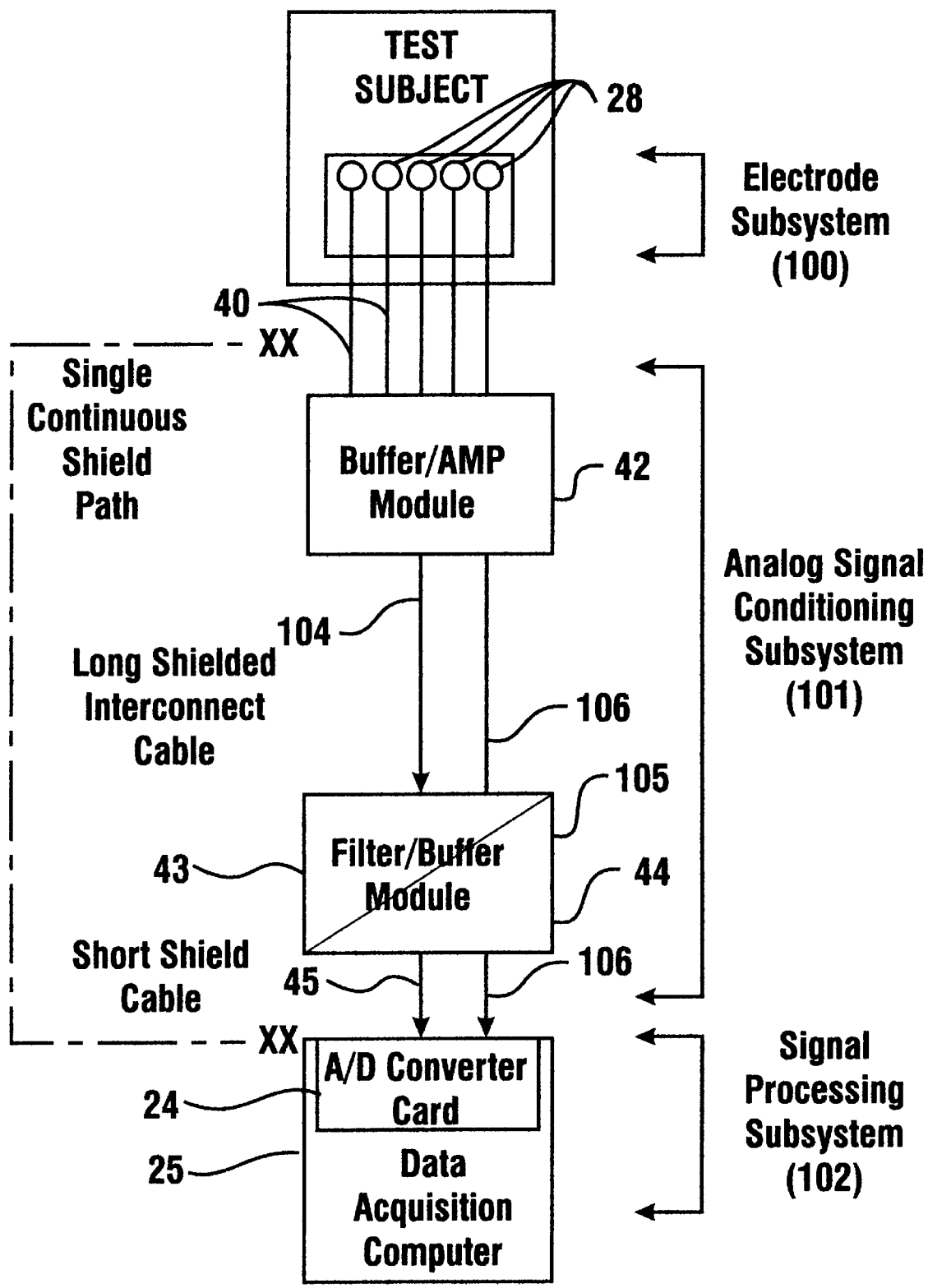
FIG. 24 is a schematic view of the apparatus of the invention, similar to that of FIGS. 2 and 4, in a modified showing of the interrelation of components of the invention.

As shown in FIG. 24 preamplifier 23 includes Buffer/Amplifier module 42 and Filter/Buffer module 105. Cable 45 connects the components of preamplifier 23 to analog to digital (A/D) converter 24 for transmission of the electrode signals for further processing and analysis.

Sensor pad 10 is applied to the back of a patient by orienting certain of the electrodes 28 to the skeletal structure of the patient. The central electrode in the top row of electrode rows 30, i.e., electrode 46 is located over the spinous process of the tenth thoracic vertebrae 18. Two other landmarks are identified in a similar manner as the sensor pad 10 overlays the mid portion of the posterior superior iliac crest (PSIS). For example, the second and fifth electrodes 33,37 respectively, in the center row of electrode rows 30 may be over the left PSIS and right PSIS. Alternatively, other landmarks may be used, such as an electrode overlying the fourth lumbar vertebrae, or other physiological reference point. This calibration information is then fed into the electronic apparatus 22 for appropriate adjustment of the voltage data received from electrodes 28 and subsequent visual display relative to predetermined displays of muscular anatomy appearing at display unit 26, in order to assure standardization of electrode placement.

Figure 8:
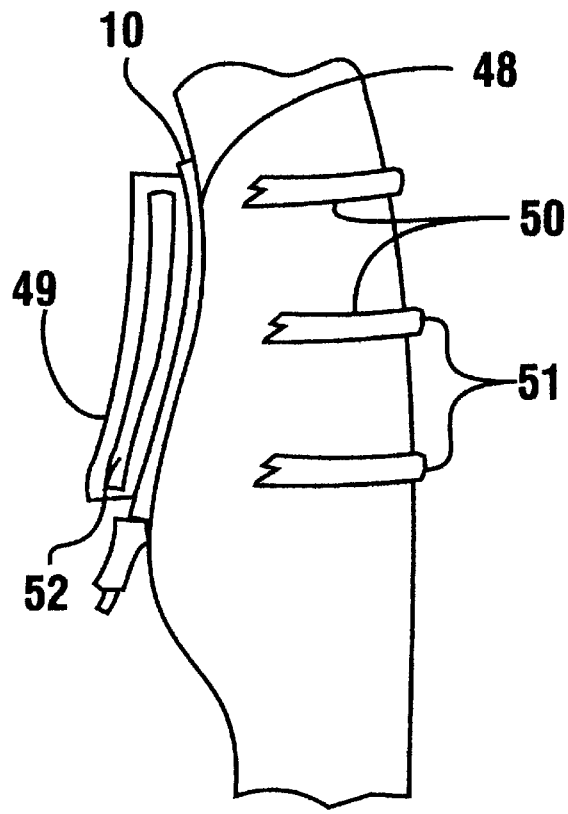
FIG. 8 is a schematic view of the lower torso of a patient with the sensor pad held in position by a retaining belt and a support pad.
Figure 9:
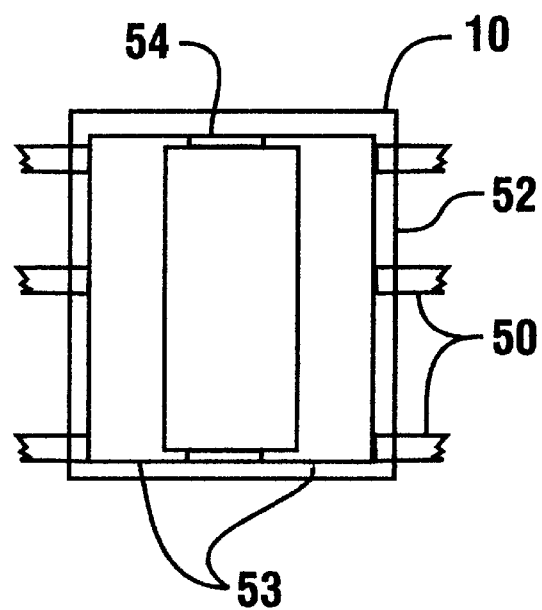
FIG. 9 is a plan view with parts removed of the retaining belt of FIG. 8, showing the support pad.

Referring now as well to FIGS. 8 and 9, there is shown in two views the mechanism for attachment of sensor pad 10 to the lower back of a human patient 48. A type of lumbar support belt 49 encircles part of the lower torso of patient 48 and is retained in place by several straps 50 of non-elastic web culminating in quick release snaps 51 at the ends thereof for adjustment and securement. Belt 49 includes a pouch therein in which is disposed a molded foam pad 52.

Pad 52 is generally rectangular in configuration and about one inch in thickness at its midpoint and tapering to about ⅛" thickness at its left and right edges. The pad has a curved inner surface generally conforming to the curvature of the lower torso of a typical patient 48 and overlying sensor pad 10 to press the latter into secure physical contact with patient 48 as straps 50 are adjusted. Preferably, belt 49 is about two inches larger than the operative portion of sensor pad 10, and pad 52 is also slightly larger than sensor pad 10, thereby to overlap the latter and assure fairly uniform pressure over the entire area of sensor pad 10 and consistent readings from electrodes 28.

Preferably, pad 52 has three parts, namely parallel vertical sections 53 and a central stiffer section 54. Pad 52 is firm, yet flexible, and thicker in the central section 54 than in the outer sections 53 as described above. In this manner a better fit is made to accommodate the contour of the human back. Support belt 49 is preferably made of non-elastic nylon material as are straps 50 to achieve a secure and reliable connection to the patient 48.

Preferably, a conductive gel is applied to electrodes 28 to enhance conductivity of the interface between electrodes and patient 48, as is well known in the art. One suitable brand of water soluble gel is that manufactured by TECA, a subsidiary of Vickers Medical, Inc.

Once sensor pad 10 has been located in position on a patient 48 and secured by support belt 49 and electrical interconnection made with electronic apparatus 22, the patient can be moved about and put through a series of different positions in order to develop a series of signal groups indicative of the underlying musculature. Typically, these positions are neutral, flexion, extension, left flexion, right flexion, left rotation, right rotation, sit, supine and prone, although various modifiers may be added to these positions. In each of the positions a scan of the electrodes 28 is made, each scan requiring only 1–10 seconds, and the signal information retained for later utilization in electronic apparatus 22.

Electrical signals from electrodes 28 are connected by way of wires 40, buffer amplifier 42, filters 43, 44 and cable 45 to analog to digital (A/D) converter 24 and then to computer 25 for analysis and conversion. A/D converter 24 is a standard converter device, one suitable version being board no. AT-MIO-64-E3, manufactured by National Instruments Company. The data from sensor pad 10 is collected in pseudo differential fashion, each electrode 28 being sampled relative to reference electrode 61 located in the center of pad 10. Subtraction of electrical data yields the wave form between the two electrodes of interest and the wave form is subjected to a root mean square (RMS) analysis over a predetermined time interval to yield a discrete number indicative of the signal strength. In one example of utilization of the signals, the RMS number is converted to a representative color indicia and that color indicia is displayed on the screen of display unit 26 in a location representative of the particular two electrodes 28 of interest.

Figure 7:
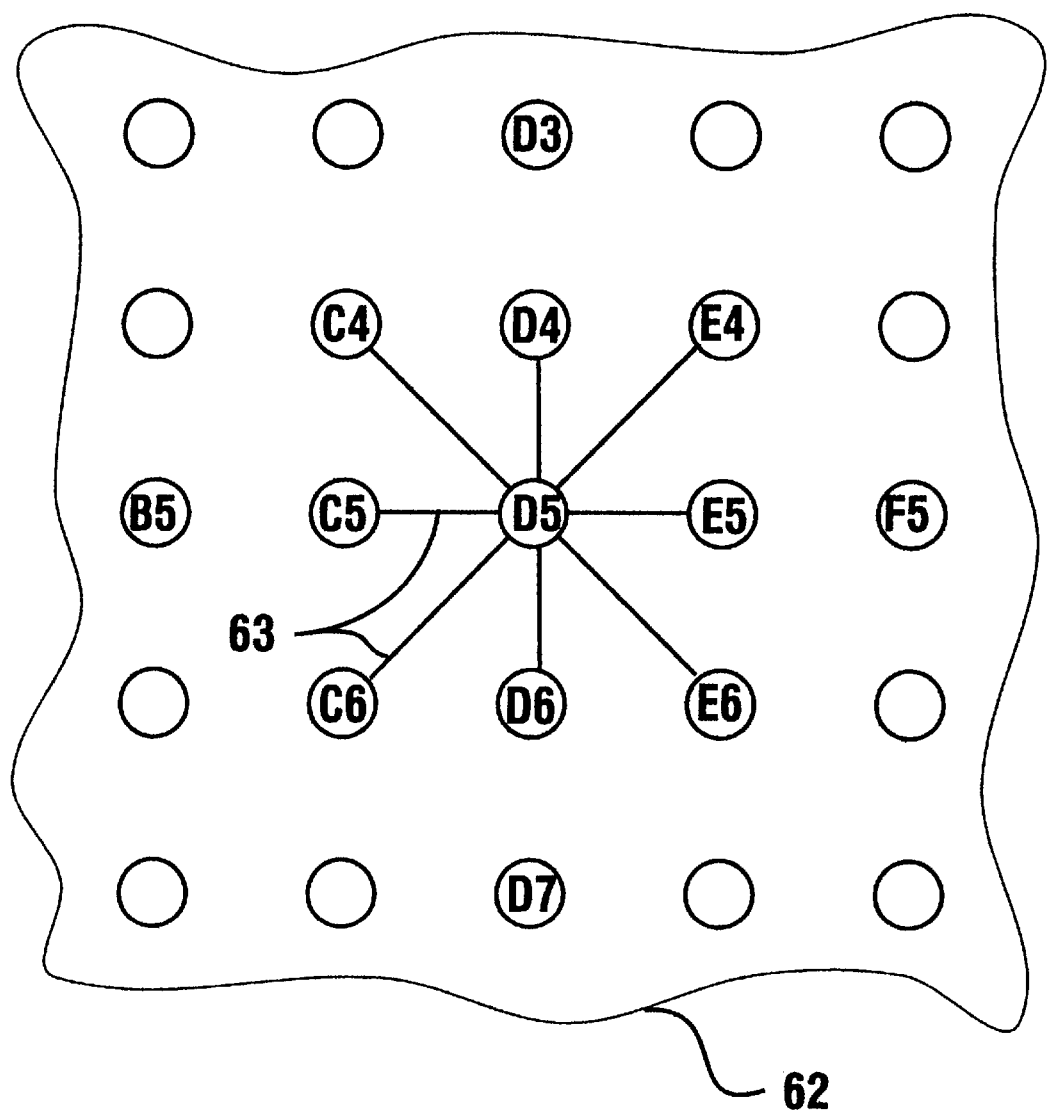
FIG. 7 is a schematic view of the screen of the display unit of the invention depicting the location of a portion of the electrodes of the sensor pad as circles and showing several interconnecting color bars.

This technique of measurement may best be seen in the FIG. 7 representation of a portion of the screen 62 of display unit 26. Here the electrode positions are represented by circles with alphanumeric designations therein, with the seven columns of electrodes 28 designated from A–G and the nine rows designated from 1–9. Thus, various electrode positions are shown, for example, as C4, D5, E6 with D5 representative of the reference electrode 61 position. Intermediate computer generated light bars or line segments 63 interconnect various ones of the adjacent electrode positions, i.e., C5-D5 and C6-D5 to represent the pattern of image generated by computer 25 and displayed at screen 62 of display unit 26.

Figure 3:
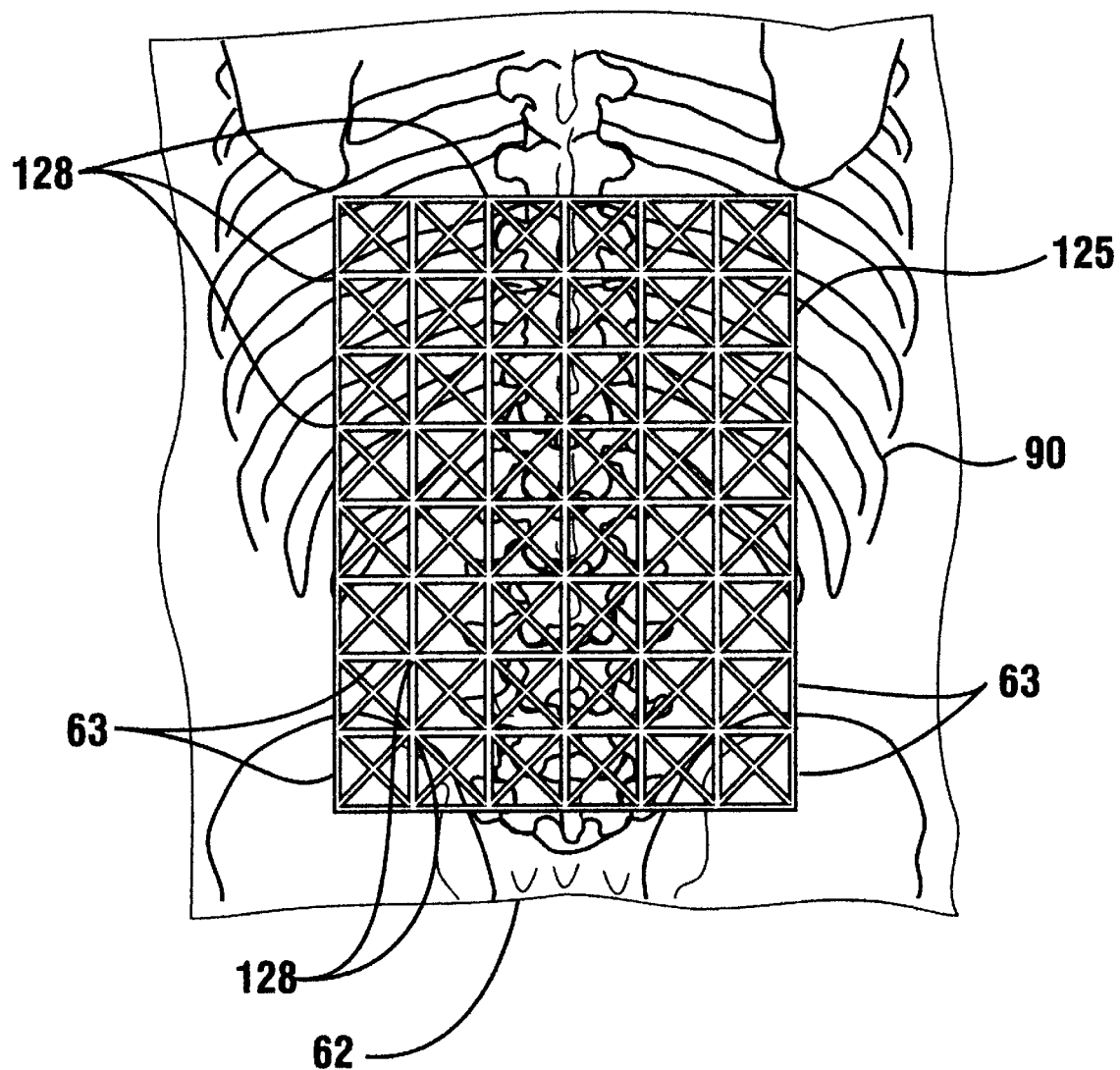
FIG. 3 is a schematic view of the screen of the display unit of the invention showing a full color bar matrix overlay in relation to the lower back skeletal anatomy of a human patient.

A full pattern display is shown in FIG. 3 wherein the screen 62 of display unit 26 shows the full array of light bars 63 interconnecting all of the electrode 28 positions, in a matrix overlying a display of the lower back skeletal anatomy 90 of the patient 48. This view demonstrates the spatial relationship among the locations of electrodes 28, the visual display of light bars 63 and the patient 48 anatomy 90 in a manner that can be readily visualized and utilized by the examining physician. It will be described in greater detail hereinafter that the light bar 63 display can be adjusted or modified by the physician, or automatically by the computer to produce effects including a more limited visual display of light bars 63, or variations in intensity, hue or colorization thereof to enhance the desired display. Further, it will be shown that instead of the skeletal structure 90 of the patient 48, various depictions of the standard musculature of the patient such as those templates shown in FIGS. 15–23 can be made to induce a correlation between the signals being obtained from the sensing electrodes and the specific musculature creating the abnormal condition affecting the patient.

In a scan of the complete array of electrodes 28, 206 color bar images are produced on display unit 26 in positions delimited by and corresponding to the positions of the electrodes 28 on sensor pad 10. Also superimposed on display unit 26 is a graphical depiction of the musculature of the lower back of patient 48 with correlation between the two being achieved by the registration process previously described where a sensor pad is located relative to the tenth thoracic vertebrae 18 and the PSIS identifying crests 12, 14.

In a preferred embodiment of the invention the diagrams of the musculature of FIGS. 15–23, may be shown at the screen of display unit 26 as a series of images, each representative of certain muscle groups of the lower back of patient 48 so that the attending physician might make a correlation between the colors which represent the strength of contraction of the muscle underneath the electrode and the particular muscles or muscle groups, and discern what muscle is causing the particular colorization patterns being produced. It is apparent as well, that it would be possible to program computer 25 to recognize abnormal signals from the electrodes 28 being polled to provide some other indication of the abnormal situation using different evaluation techniques. It is also apparent that the signals collected from electrodes 28 can be stored in a database and processed in different ways, perhaps at later times or printed out in hard copy, if this is a desired result. The capture of data from all of the electrodes 28 occurs substantially simultaneously and is stored in computer 25 for manipulation in a myriad of possible ways, only certain of which are described herein.

Figures 10, 11:
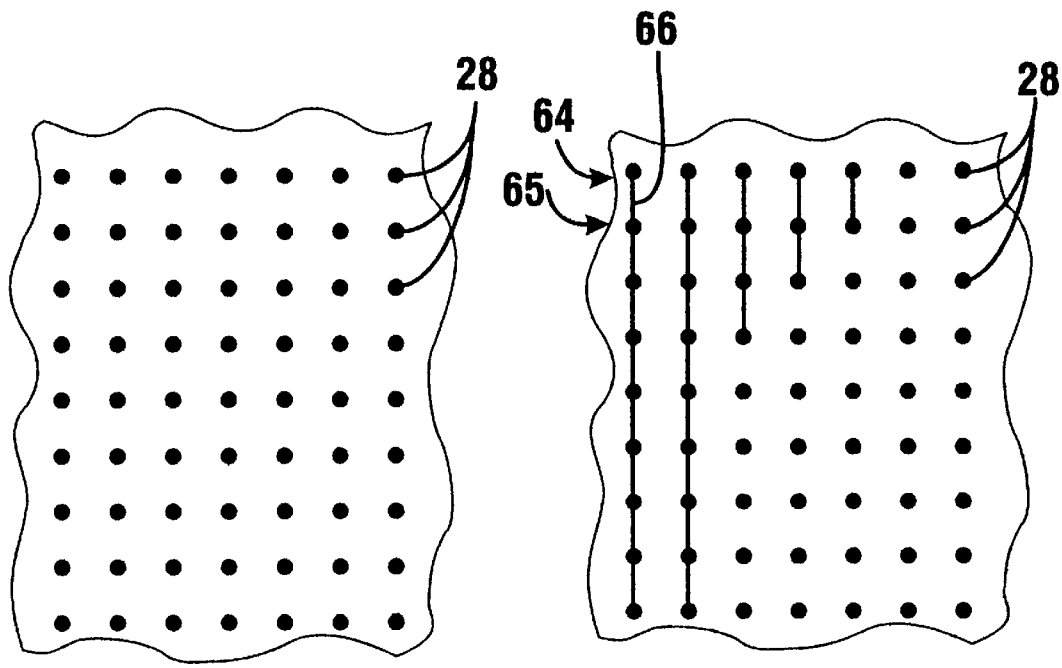
FIGS. 10–13 are schematic views of the screen of the display unit showing various configurations of color bar displays.

Referring now to FIGS. 10–13, there are shown several variations of the techniques for monitoring and analysis of the electrical signals derived from electrode 28. As previously described, each electrode 28 is scanned relative to reference electrode 61 to develop a signal representative of the voltage level detected at the site of the particular electrode, and data representative of the signal retained in computer 25. In further processing of the signals, each signal may be compared to that of other electrodes to develop signal patterns representative of the muscle condition being evaluated. For example, FIG. 10 is a representation of signals developed at sensor pad 10 when only a depiction of a discrete color dot is made at the location of each electrode 28, with no showing of color bars. This display might be most useful in achieving a desired registration between electrode 28 display and the skeletal structure 90 display.

FIG. 11 describes a first variation for analysis of the signals where the signal of each electrode 28 in the first row 64 is compared to the corresponding electrode 28 in the same column, in the second row 65 to develop a resultant signal, represented at display unit 26 as a bar 66 joining the location of the particular electrodes. In this manner a full pattern of vertical bars 66 is developed, although only a portion is shown, with each being a unique color and representative of the signal comparison at each electrode pair. Such arrangement of color bars 66 may be displayed juxtaposed to patterns of muscle structure as previously described, and likely is more useful in displaying an association with muscles or muscle groups which are oriented generally vertically in the back of the patient.

Figures 12, 13:
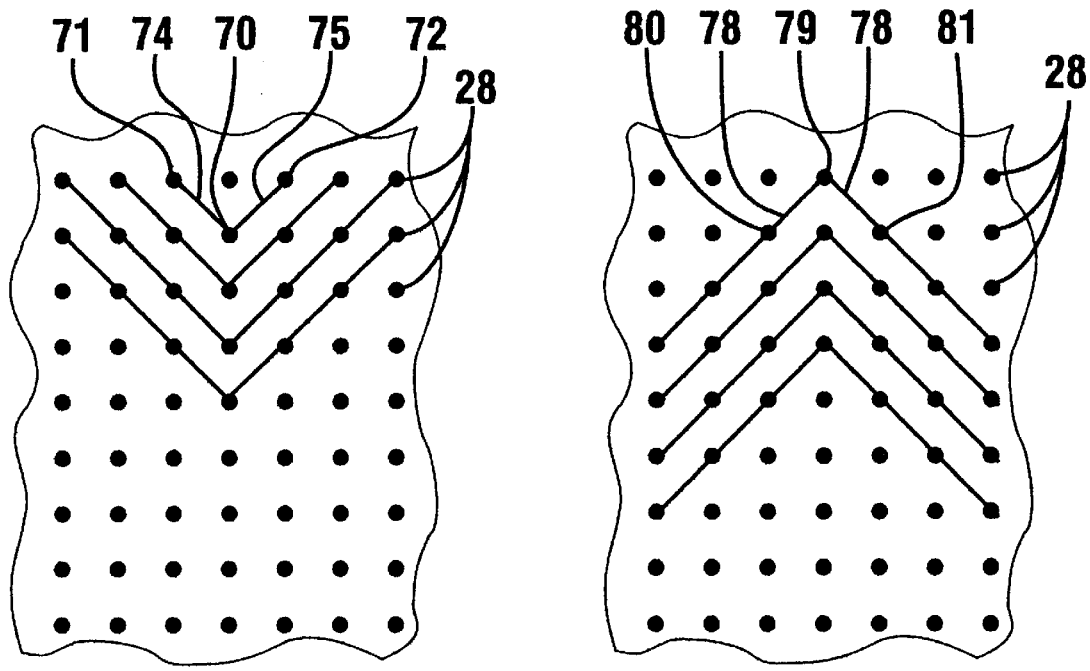
Figure 14:
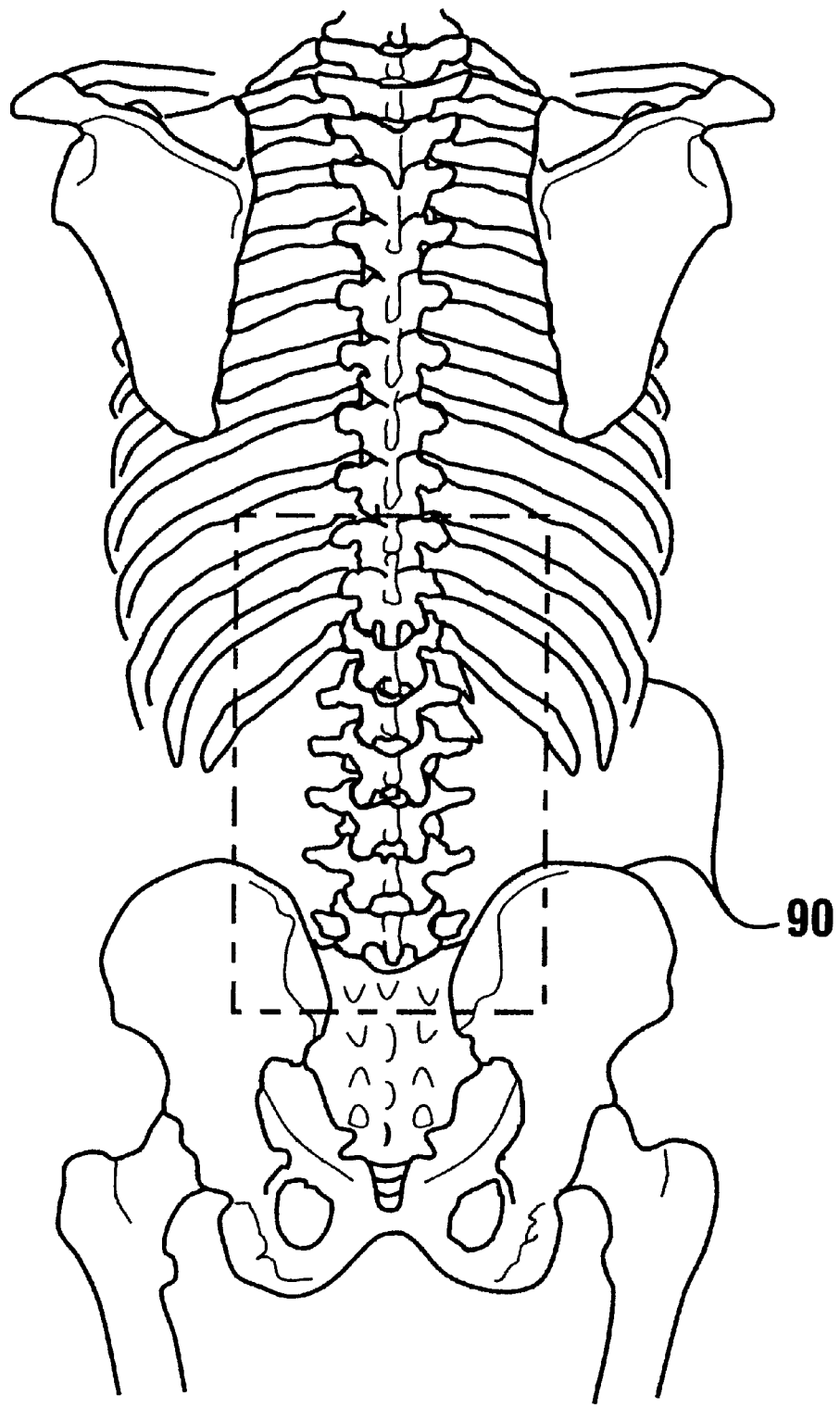
FIG. 14 is a schematic diagram of skeletal anatomy associated with the lower back of a normal human patient.
Figure 15:
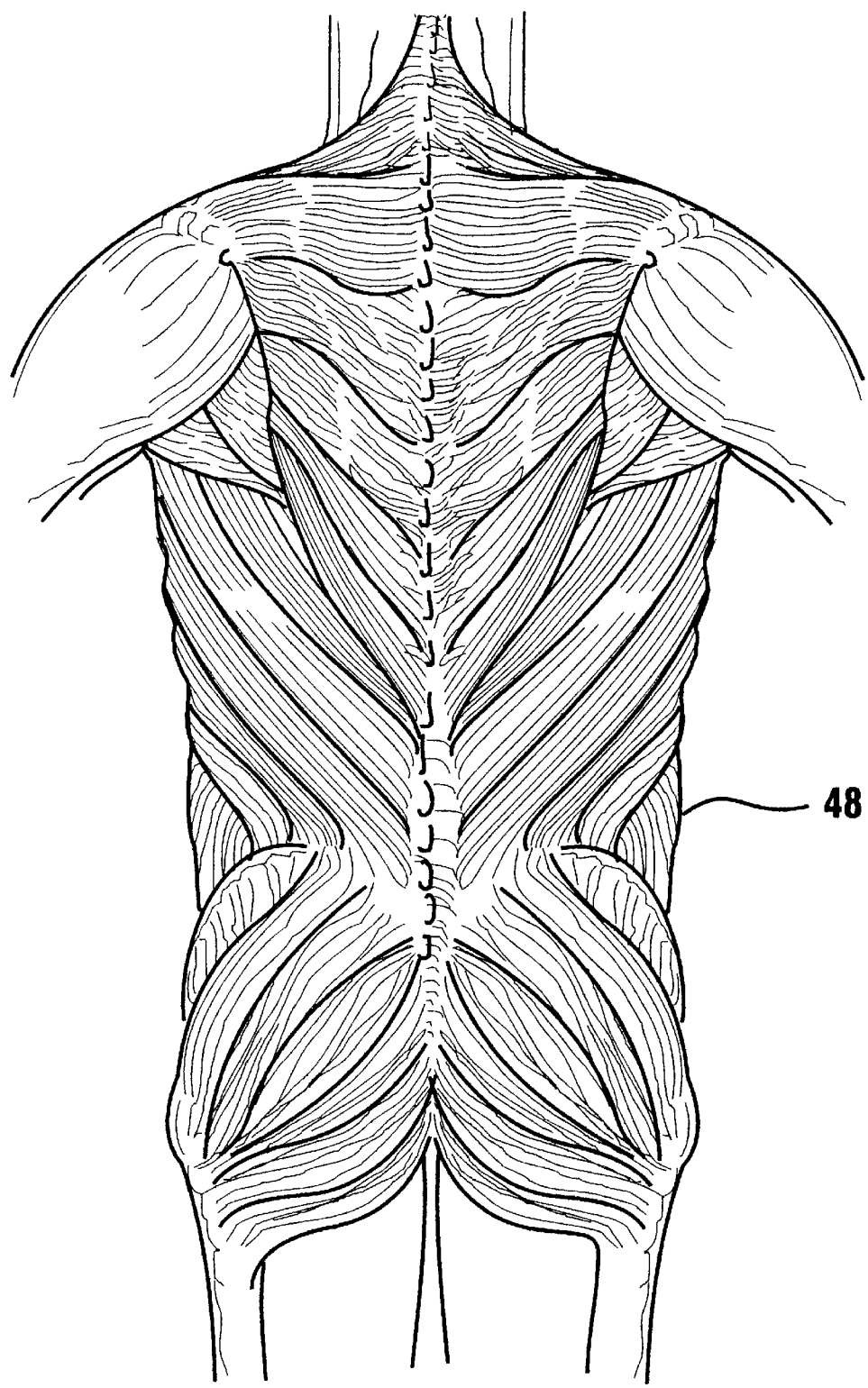
FIGS. 15–23 are schematic diagrams of various groups of musculature of a normal human patient shown in relation to the skeletal anatomy of FIG. 14.
Figure 16:
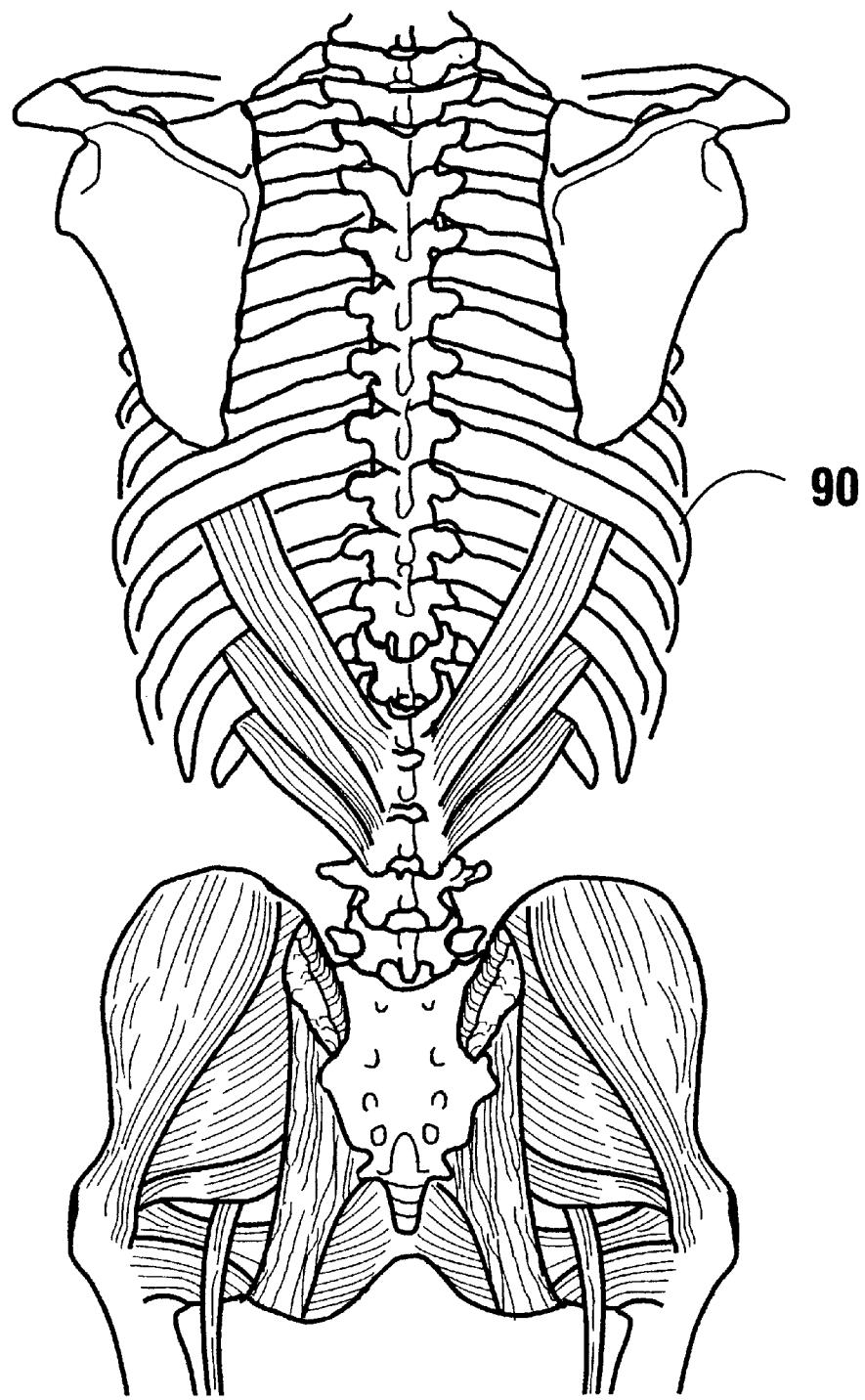
Figure 17:
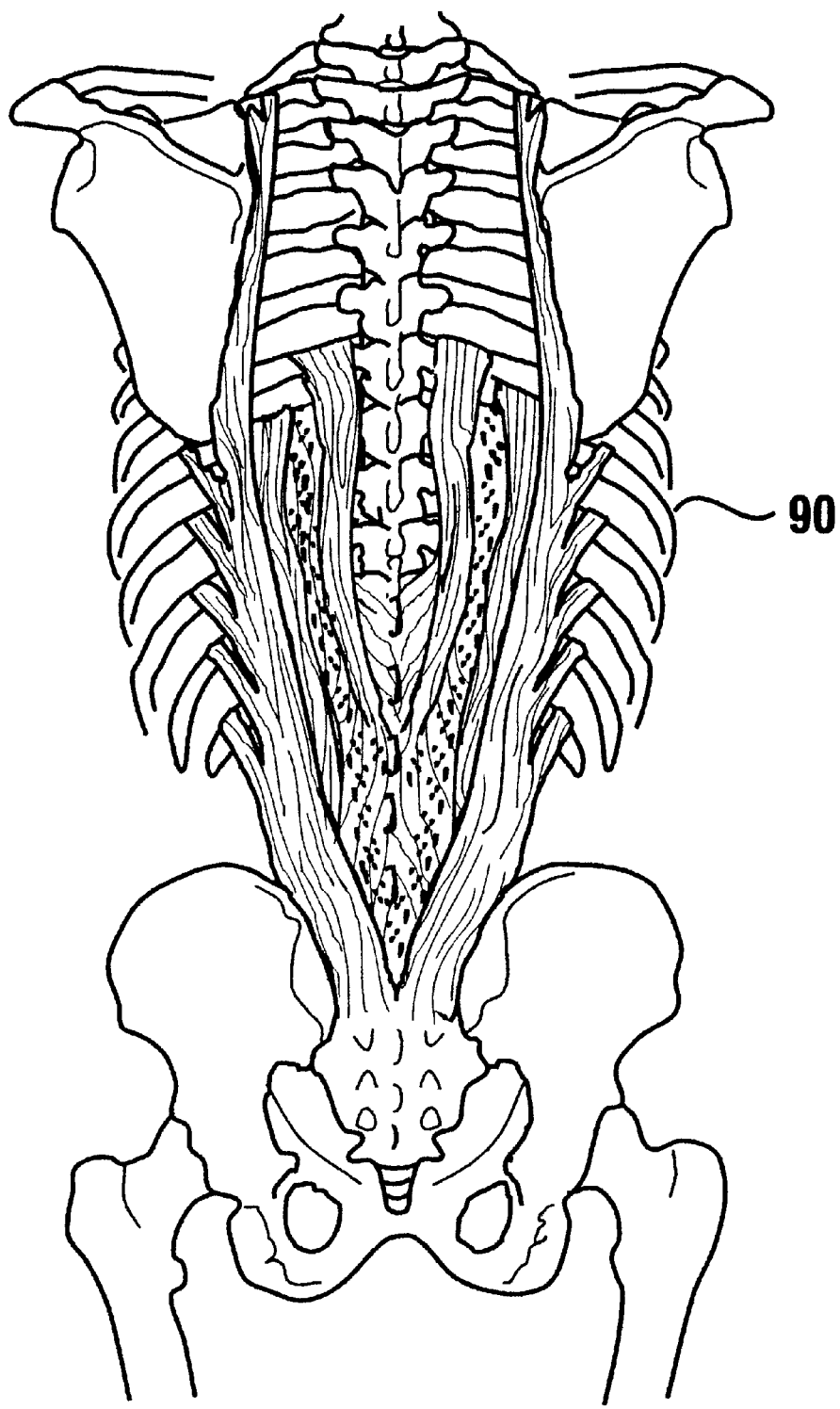
Figure 18:
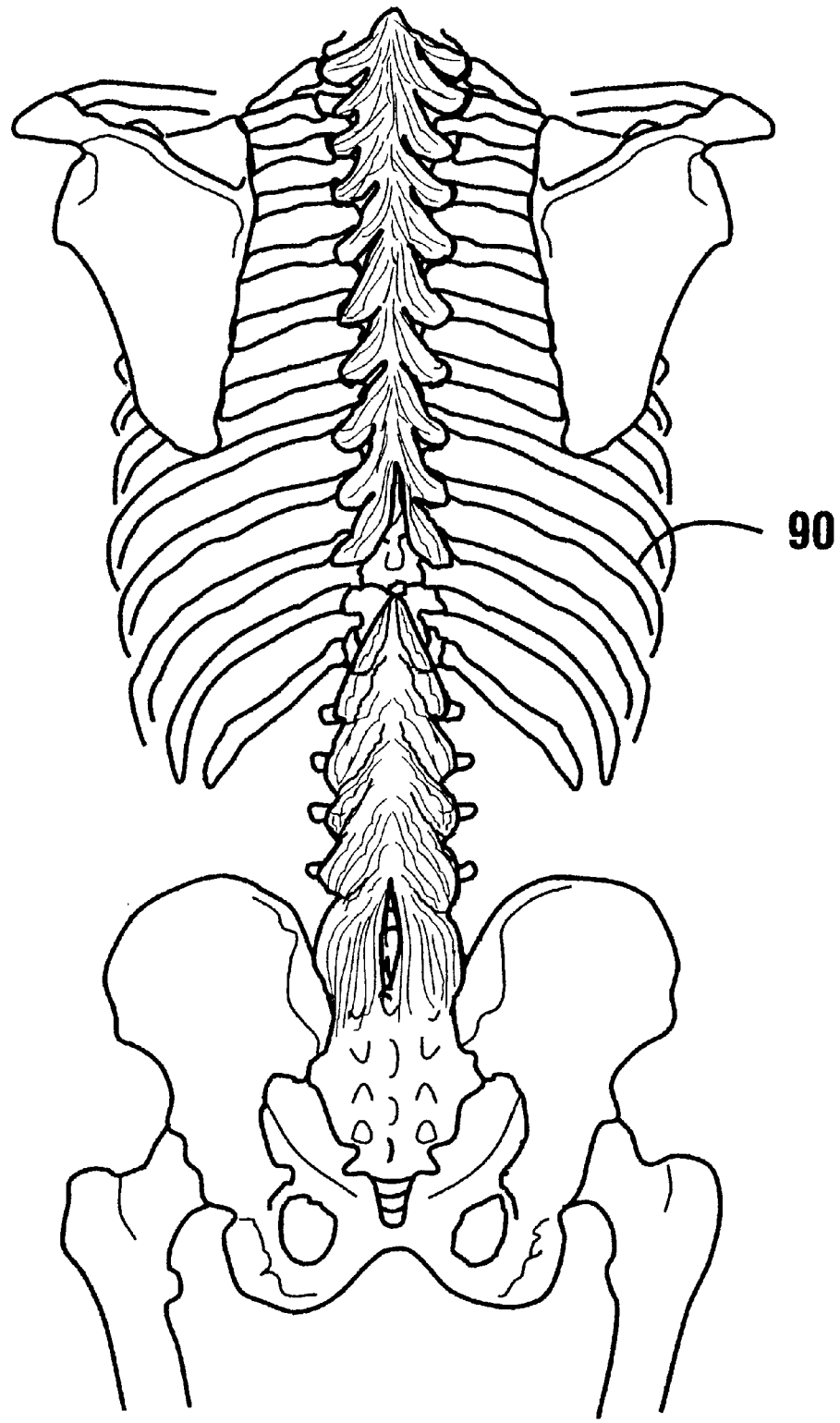
Figure 19:
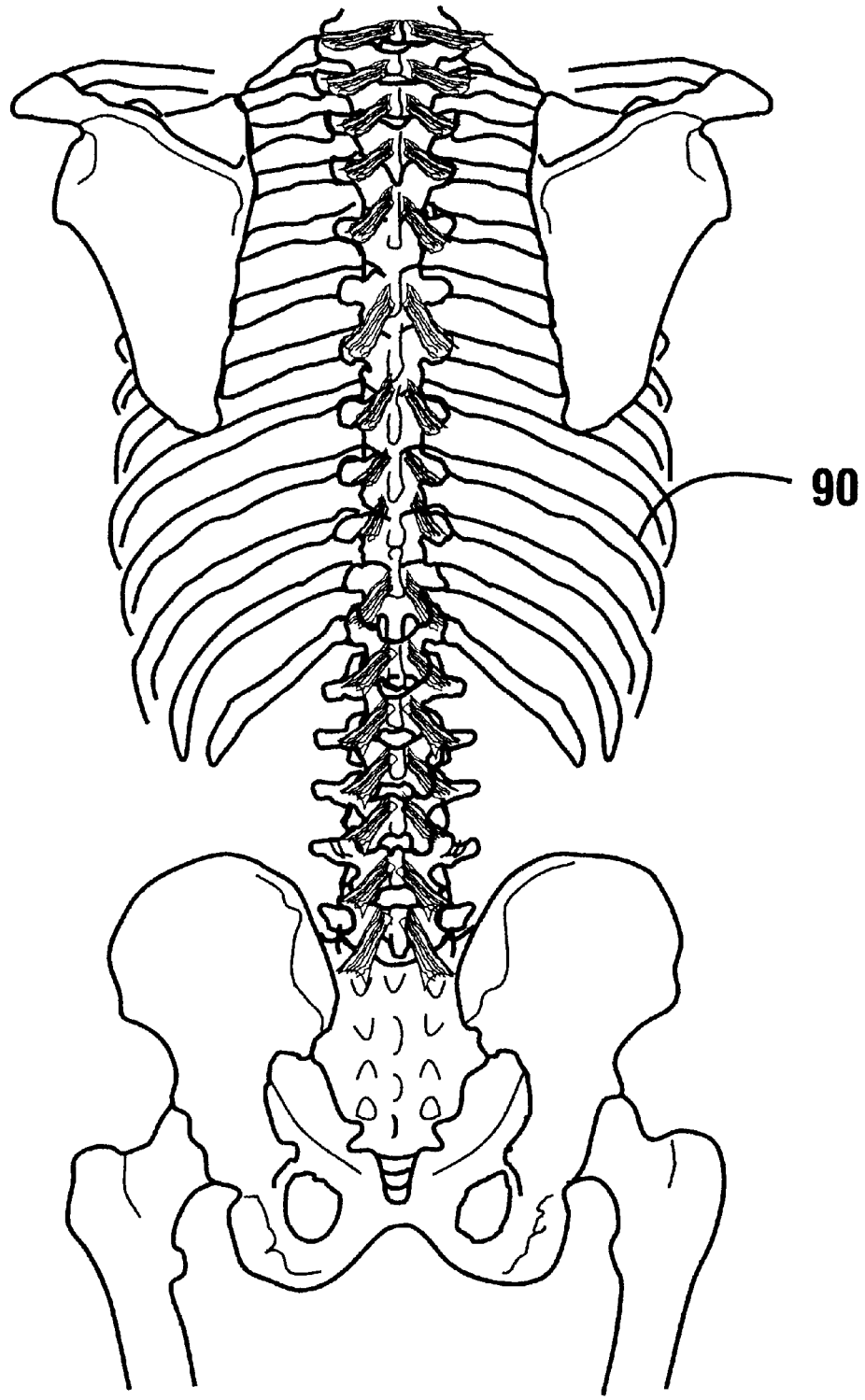
Figure 20:
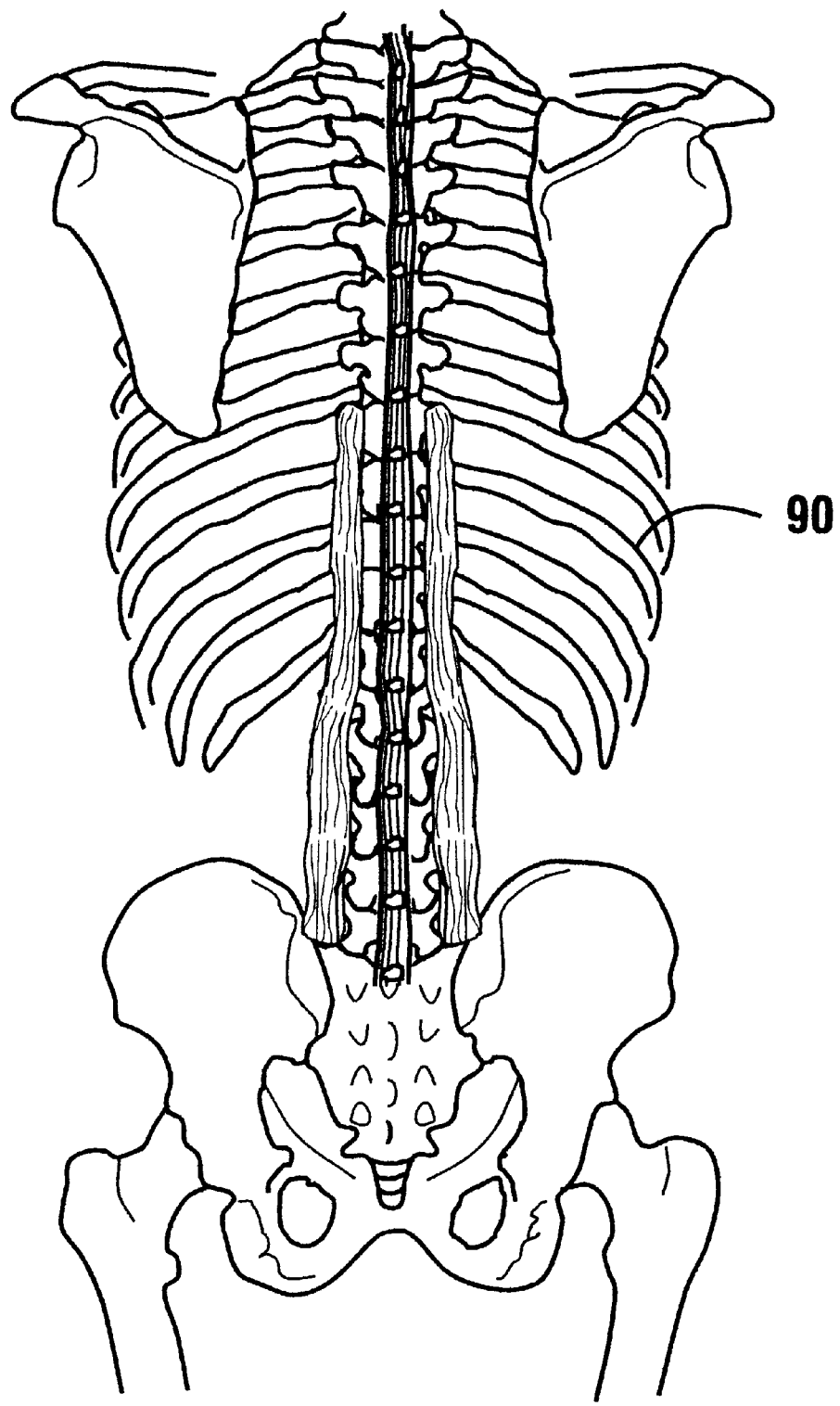
Figure 21:
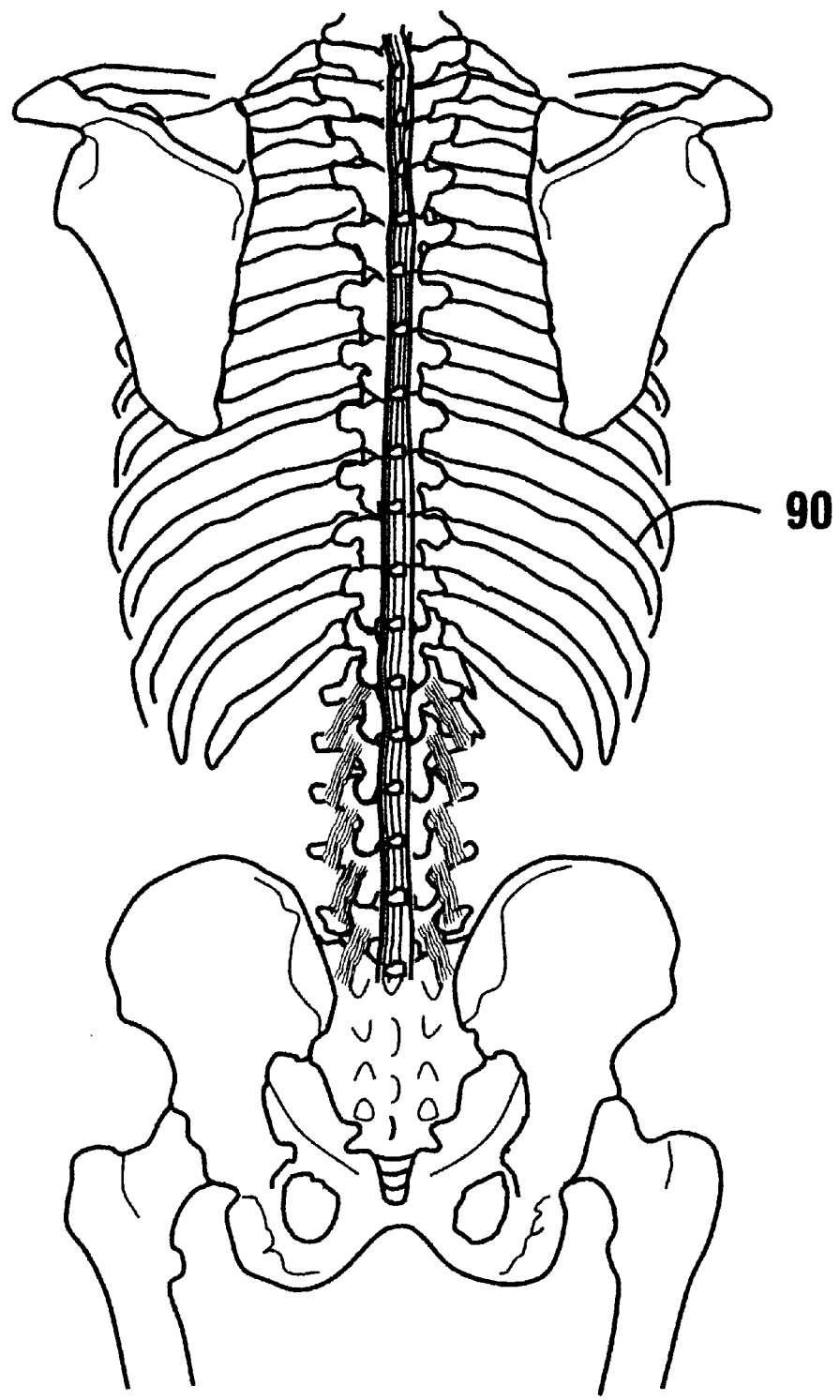
Figure 22:
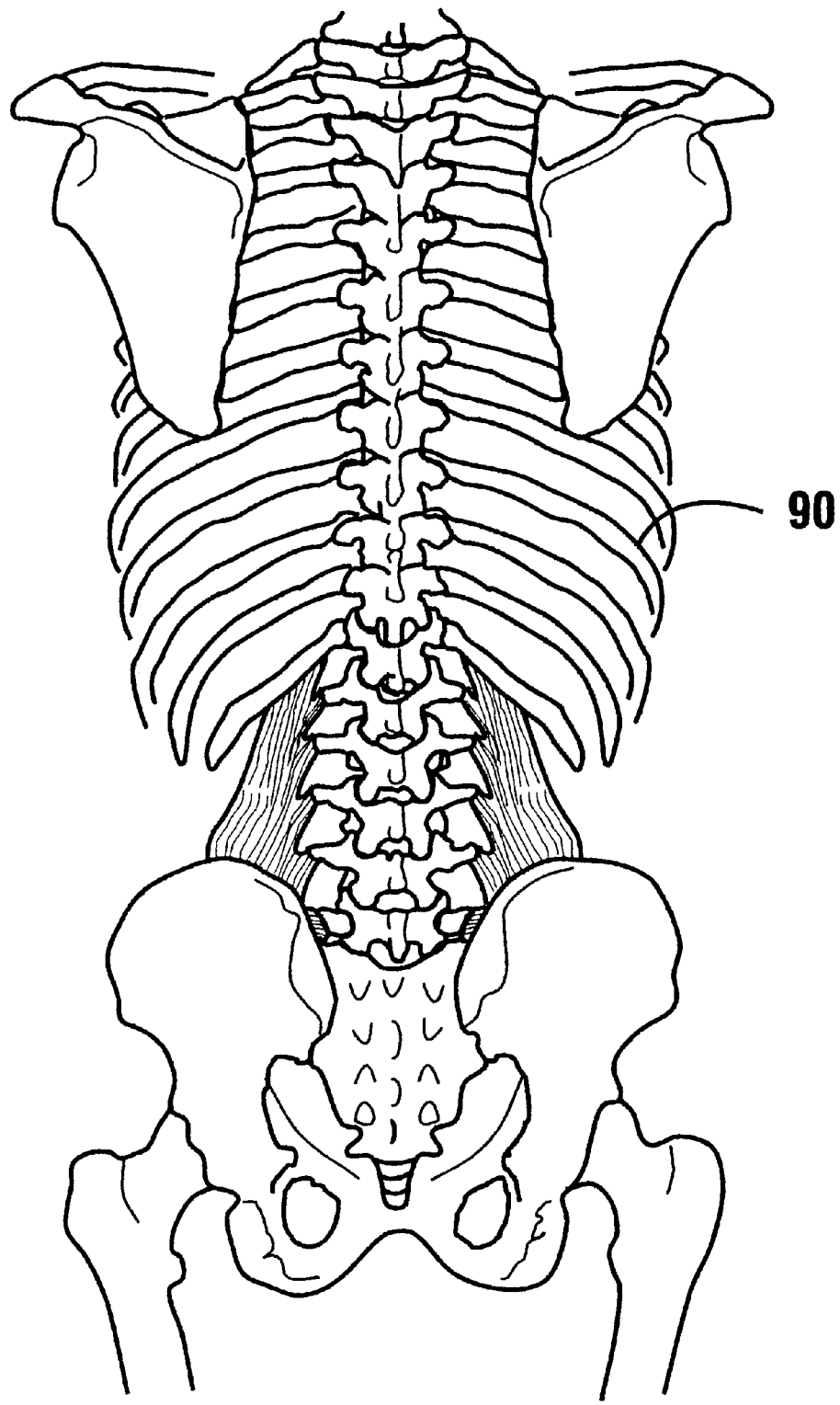
Figure 23:
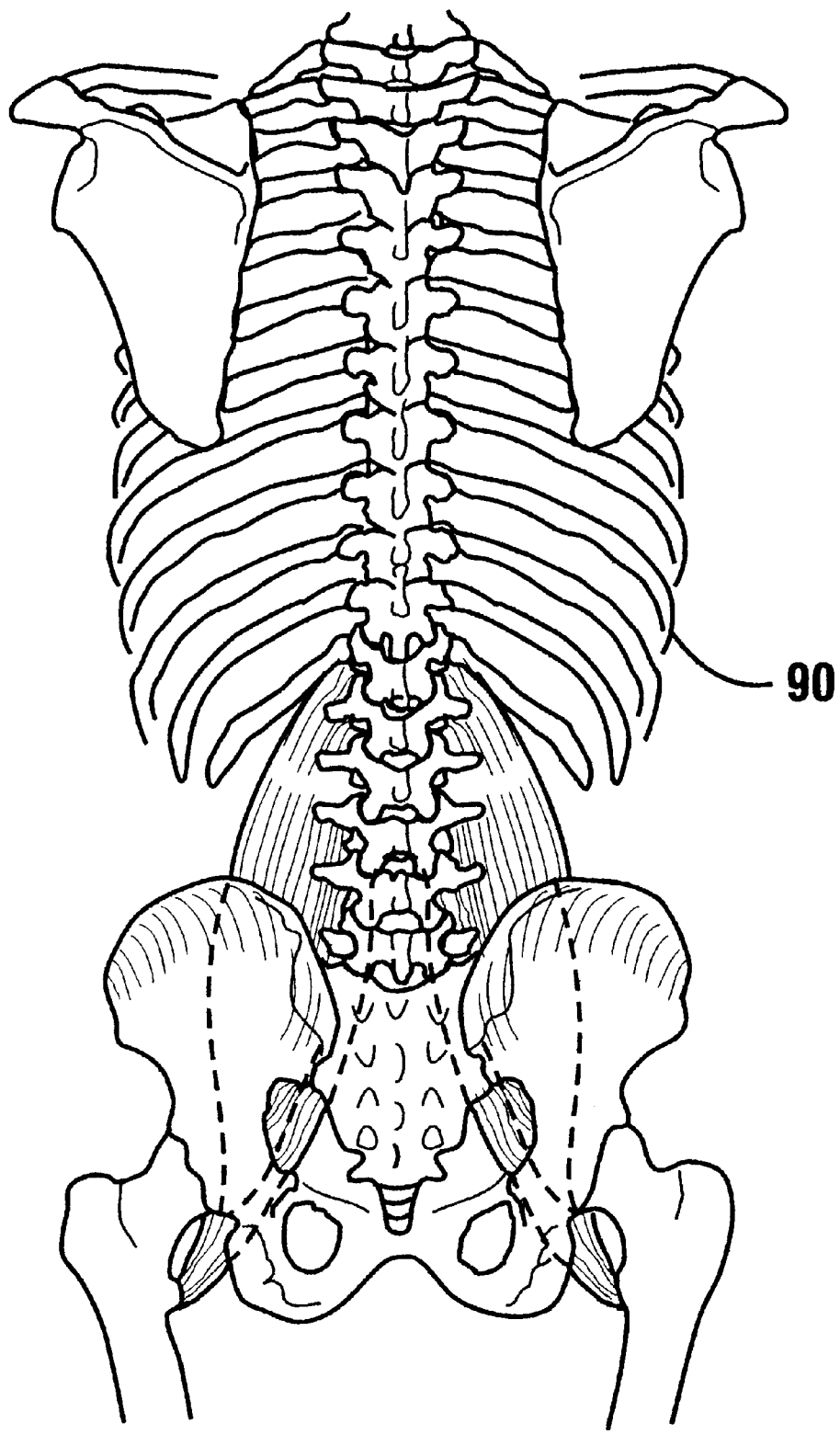

FIGS. 12 and 13 represent yet other variations of signal analysis wherein different herringbone patterns of signal are derived. In FIG. 12, for example, the signal of center electrode 70 in the second row, center column (D2) is compared with electrodes 71, 72 in the first row and adjacent columns (C1) (E1) to develop intermediate color bars 74, 75 respectively, indicative of the comparison of the electrode signals. Further color bars corresponding to bars 74, 75 are developed throughout the array of electrodes 28 to achieve an overall pattern for display at display unit 26. Again, only a portion of the display is depicted in FIG. 12, for purposes of clarity.

FIG. 13 is yet another variation of a display that may be produced using this technique of monitoring. Here an inverted herringbone pattern consisting of color bars 78 is achieved when the signals from electrodes 28 are compared in the described pattern. For example, electrode 79 in the first row, center column (D1) is compared to electrodes 80, 81 in the second row in adjacent columns (C2) (E2) to produce the intermediate color bars 78. When extended throughout the array of sensor pad 10, a colored herringbone pattern of color bars 78 is achieved for comparison with muscle pattern displays shown in association therewith.

It is apparent that still further comparisons can be made of the signals obtained from electrodes 28, for example to compare the signal of each electrode 28 with the signals of all adjacent electrodes 28, and electronically summarize the information obtained and to produce a representative color pattern of the results for visualization at the face of display unit 26.

Similarly, it is apparent that the resultant electrical signals from electrodes 28 and the resultant color information can be shown at display unit 26 in different formats to emphasize the relationship between developed signals and the underlying muscle structure. With a suitably high speed computer 25, the images of differing muscle structures can be shown in association with the color patterns as directed by the physician to provide a correlation between the colorization and the abnormal muscle elements.

Figure 25:
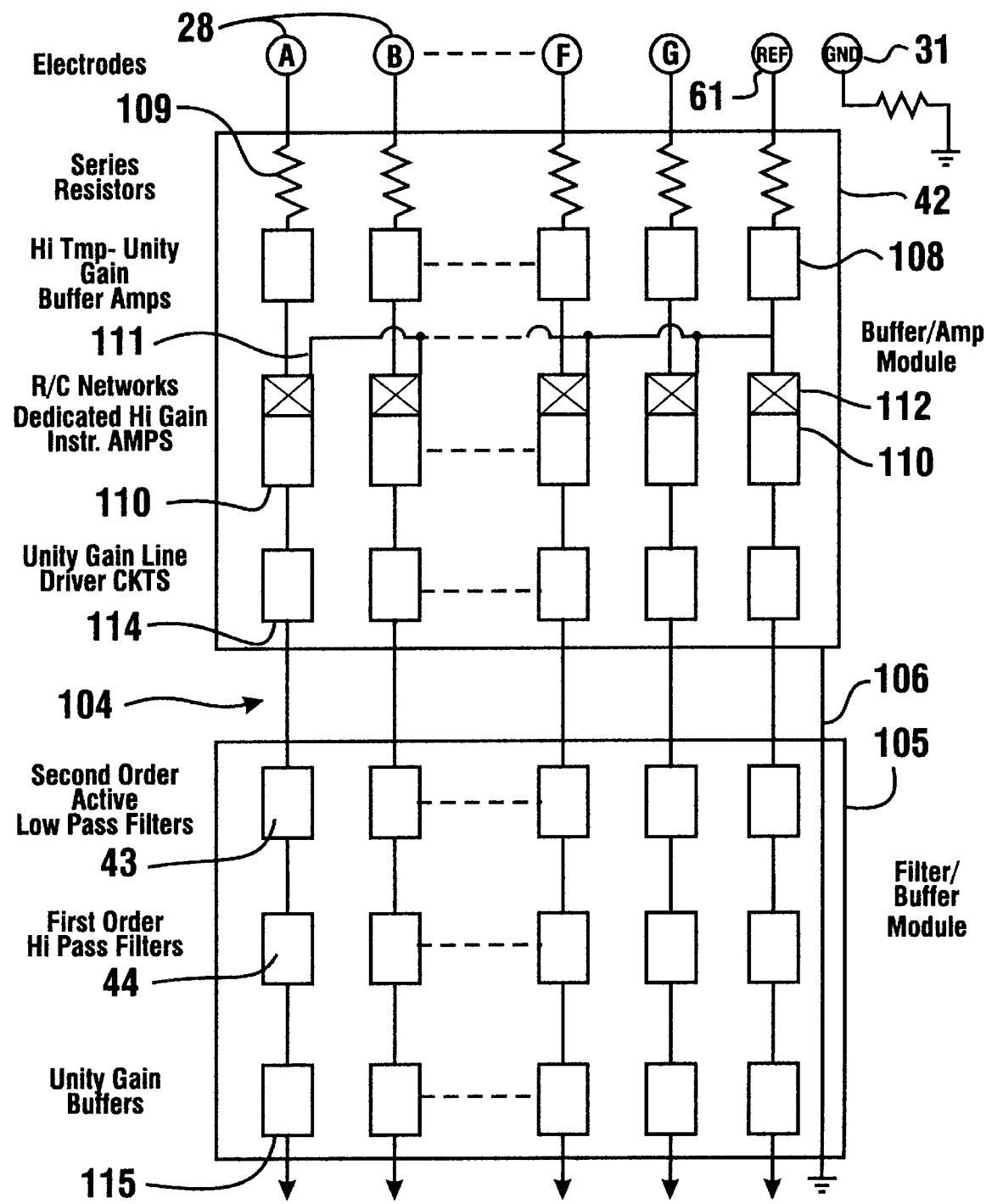
FIG. 25 is a schematic view of the components comprising the Analog Signal Conditioning Subsystem of FIG. 24.

Referring now to FIGS. 24 and 25, there is shown in more detail the components comprising the analog and digital signal portions of the invention including electrode subsystem 100, analog signal conditioning subsystem 101, and signal processing subsystem 102. Electrode subsystem 100 comprises the array of sixty-three electrodes 28, only a few of which are shown and labeled as A, B, F, G, Ref. and Gnd. in correspondence with previous descriptions. Wires 40 connect electrodes 28 to buffer amplifier 42, shown in block form on FIG. 24 and in more detail in FIG. 25.

A long shielded interconnect cable 104 connects the outputs of buffer amplifier 42 to more remotely located Filter/Buffer module 105 which includes low and high pass filters 43, 44. In turn, a short shield cable 45 completes the analog signal portion, being connected to analog to digital converter card 24 in computer 25, the latter components being essential parts of the signal processing subsystem 102. As indicated, a single continuous shield path, depicted by dashed lines 107, is established between Buffer/Amplifier module 42 and computer 25, assuring that minimal interference is generated in the signals of interest from extraneous sources.

The enclosures used for the Filter/Buffer module 105 and the Buffer/Amplifier module 42 are shielded with a layer of conductive material. All enclosure shields are connected in series with the interconnect cable shields, resulting in a single continuous shield path from the Buffer/Amplifier input connector to the data acquisition computer 25 chassis ground.

The array of electrodes 28 mounted on sensor pad 10, as previously described, must conform to the human back, ensure consistent electrode impedance with the skin, not interfere substantially with patient movement, and be easy to clean and reuse. The electrodes 28 are preferably in a nine row by seven column configuration and the sensor pad 10 is preferably held in place with a fabric brace with or without pressure sensitive adhesive.

The analog signal conditioning subsystem 101 provides buffering, voltage amplification and analog filtering for the array of electrodes 28. One electrode in the array is designated as the reference electrode 61, and all other electrode voltages are measured with respect to the reference electrode 61.

Each of the electrode 28 signals is connected by way of wires 40 to high impedance, unity gain buffer amplifiers 108 by way of a 10K Ohm series resistor 109. The purpose of resistor 109 is to provide a measure of resistive isolation for safety purposes, as well as to increase the electrostatic discharge (ESD) immunity of the amplifier.

Following the buffer amplifiers 108, each channel has a dedicated high gain instrumentation amplifier 110. The inverting input of each instrumentation amplifier 110 is connected to the buffered signal from the reference electrode channel as shown by connector 111. Thus, the output of each instrumentation amplifier 110 represents the voltage of a given electrode with respect to the reference electrode 61. RC networks 112 connected to the inputs of the instrumentation amplifier 110 serve as low pass filters to block unwanted high frequency signals. The outputs of the instrumentation amplifiers 110 feed into unity-gain, line-driver circuits 114 that are capable of driving the capacitive load of the long shielded interconnect cable 104, without oscillation.

The ground electrode 31 is connected to the patient and is connected to ground through a resistor. In the preferred embodiment electrode 31 is connected to the analog signal ground on the digital converter card through a one million Ohm resistance. The preferred form of the analog to digital converter card 24, is a sixty-four channel multiplexed converter capable of operating in pseudo-differential input mode. The Buffer/Amplifier module 42 and Filter/Buffer module 105 are each connected to ground as represented by line 106.

Each of the sixty-three signal inputs into Filter/Buffer 105, via cable 104, is connected to a second order active low pass filter 43. The output of low pass filter 43 is connected to the input of first order, high pass filter 44. The output of each high pass filter 44 is connected to unity gain buffer 115 that is capable of driving the capacitive load of the analog to digital converter card 24 interconnect cable 45, without oscillation. Electronic power for Filter/Buffer module 105 is provided by an external linear power supply. Filter/Buffer module 105 provides power for Buffer/Amplifier module 42 via the interconnect cable 104. Ground sense line 106 from the Buffer/Amplifier modules 42 passes directly through the Filter/Buffer module 105.

Figure 26:
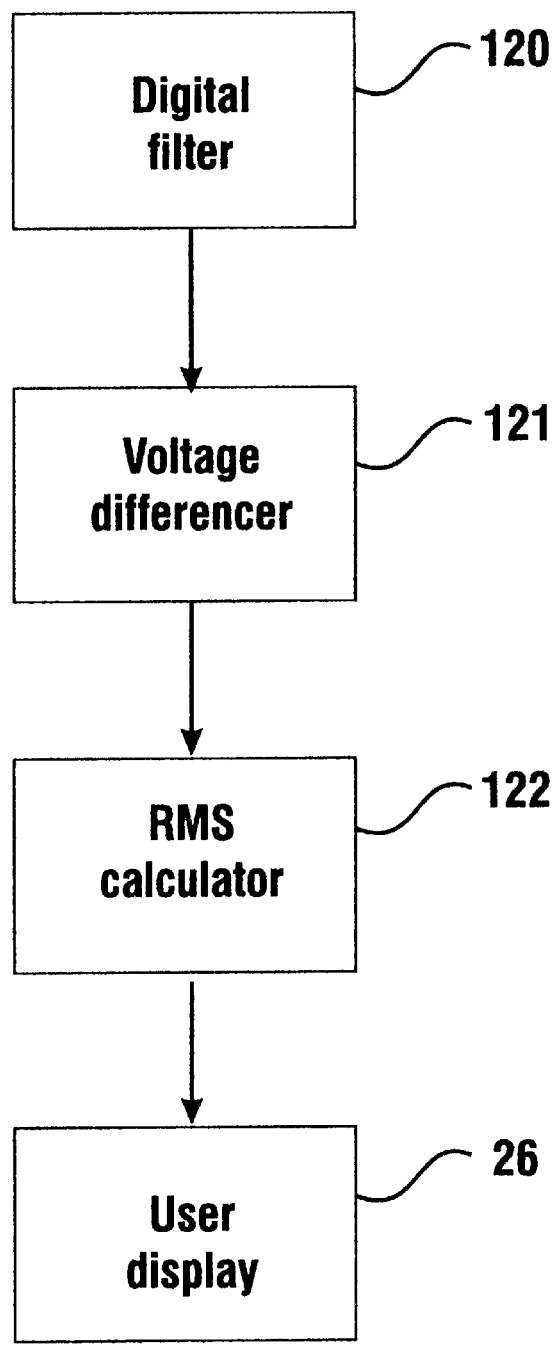
FIG. 26 is a schematic view of the components comprising the Signal Processing Subsystem of FIG. 24.

Signal processing subsystem 102 is shown in block diagram form in FIG. 26 and consists of the major elements of a digital filter 120, voltage differencer 121 and RMS calculator 122. First, digital filtering techniques are used to reduce noise on the measured signal. Next, a voltage differencer 121 determines the voltage waveform between all adjacent electrodes 28. Finally, the root-mean-square (RMS) voltage between all adjacent electrodes is calculated and used to characterize the level of muscle activity between adjacent electrodes. The signal processing subsystem is preferably implemented in software on a PC-compatible computer 25.

The digital signal conditioning system consists of high pass, low pass and band-cut digital filters incorporated into the data analysis software. The high and low pass filters are designed to reject signals outside of the frequency range of interest, and have amplitude rolloffs of 80 dB/decade. The primary purpose of these digital filters is to block common-mode error signals introduced near the corner frequencies of the analog filters. The band-cut or notch filter drastically reduces 60 Hz signals, in order to eliminate unwanted pickup of power line emissions. In one preferred form of the invention oversampling is used which interpolates additional pseudo sample points between actual sample points to improve performance of filters, for example to achieve good frequency discrimination in the 60 Hz notch filter. In one preferred embodiment 10× oversampling is used.

The output of the electrode voltage data acquisition subsystem consists of a set of voltage waveforms of each electrode 28 with respect to a particular reference electrode. The voltage differencer 121 computes, the voltage waveform between each pair of adjacent electrodes (vertically, horizontally and diagonally) by differencing the voltage waveforms for the two adjacent electrodes. RMS calculator 122 provides the RMS value of each adjacent electrode pair waveform as a scalar number which is computed from the waveform using a conventional RMS calculation.

The user display subsystem 26 presents the processed data to the practitioner in a readily understandable format. The data is displayed as images on a screen or other visual output device. A digitized illustration of a muscle layer in the human back as shown in FIGS. 14–23 is used as the background of the image. The user may select any muscle layer as the image background. A computer generated image 125 of the processed electrode 28 data is overlaid on the selected background illustration, and is spatially registered to that image.

The electrode data image 125 consists of colored lines or light bars 63 drawn between the locations of each of adjacent electrodes 28, which are at each intersection 128 of each of the seven vertical columns and nine horizontal rows of light bars 63 as shown in FIG. 3 and as has been previously described. The color of each line 63 indicates the value of the RMS voltage between the adjacent electrodes. The user can dynamically specify a maximum RMS value and a minimum RMS value, which are used to map voltages to colors. The resulting display is thus a false-color RMS, voltage gradient field display, and is overlaid on and registered to the underlying muscle layer illustration.

Figure 27:
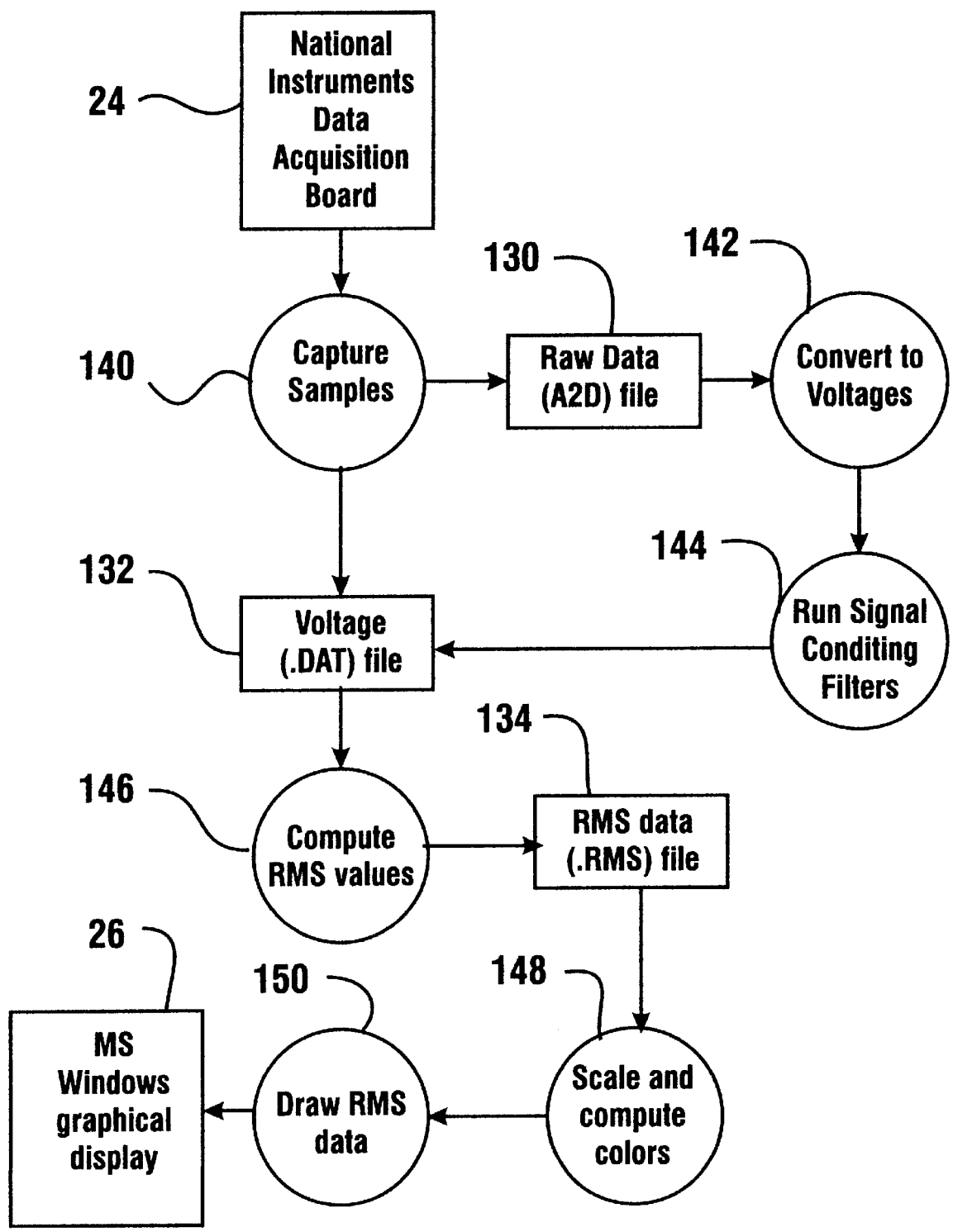
FIG. 27 is a logic diagram showing the data flow in the software of the system.

The software architecture of the signal processing system 102 is shown schematically in FIG. 27 as a diagram of the main data flow in the software. Essentially, this is a linear flow of computations, each of which takes a datum or file as input and generates a datum or file as output. Three types of data files are generated and stored and once created may be opened and displayed many times at later dates. The data files are described as well in FIG. 29 and comprise the Analog to Digital (A2D) file 130, Voltage (DAT) file 132 and Root Mean Square (RMS) file 134.

The format of header 135 for each of the files, 130, 132, 134 is depicted in FIG. 28 and in one embodiment contains information in an identical ASCII header format consisting of version information 152, patient information 154, which are the vital statistics on the patient being diagnosed, pad information 155 which provides specifics of sensor pad 10, calibration information 156, data acquisition settings 157 and display settings 158. The calibration information is derived after the sensor pad 10 location is determined on the back of the patient, being input by the operator to specify where certain parts of the patient's back are in relation to the electrodes on the pad, as previously described.

The A2D files 130 contain the actual analog to digital values at the output of analog to digital converter 24 which are collected during a test. Computer 25 scans all electrode channels rapidly enough to reconstruct the analog signal at all frequencies of interest. In one embodiment the minimum frequency of interest is about 30 Hz and the maximum about 150 Hz. The structure of the A2D files 130 is shown in FIG. 29 with each scan sample being stored in a two byte word in little endian format. The files 130 contain the analog to digital value and a header 135.

The voltage files 132 contain the voltage data from a test, after it has been converted from analog to digital values to voltages and signal conditioning filters have been applied. The voltage files 132 of this embodiment also contain the header 135 followed by the voltage values in the format shown in FIG. 29, each sample being stored as an IEEE double floating point value.

The RMS files 134 contain the RMS values of the differences between the voltage waveforms of adjacent electrodes 28. During display of an RMS file 134, the values can be mapped to colors and displayed as colored line segments or color bars 63 at display unit 26. Again, the RMS files 134 contain header 135 followed by the RMS information. The RMS voltage difference is calculated for each pair of adjacent electrodes 28. The row and column position of each of the two electrodes are also stored in the format described in FIG. 29. Also included is information of the minimum and maximum RMS value in each scan and the total number of adjacent electrode pairs.

Summarizing then, the flow of data as depicted in FIG. 27 occurs as computer 25 generates signals to capture samples 140 from data acquisition board 24 at the input to computer 25 to create raw data or A2D files 130. Computer 25 then acts to convert the signals to voltage at 142 and run signal conditioning filters 144 to create voltage files 132. Computer 25 is then programmed to compute the RMS values at 146 and create the RMS data file 134. Subsequently, computer 25 operates to scale and compute color values at 148, and then to draw the RMS data at 150 and eventually provide the color bar matrix 125 depicted in FIG. 3.

The general architecture for the software operated in computer 25 can be seen from the source file 160 structure depicted in FIG. 30. The document view and visual interface 161 contain main initialization, menu and toolbar commands, message handlers and document/view commands. Dialog popups 162 allow for entering patient information, calibration information and the like and for editing various parameters. Further files include data acquisition, filtering and calculation 163, reading and writing header information and data 164, utilities 165, and bitmaps, icons and resource files 166. These routines are fairly typical for handling the information flow in the ways specified previously and are well understood in the art, not requiring detailed description herein.

Although certain embodiments of the present invention have been disclosed and specifically described herein, these embodiments are for purposes of illustration and are not meant to limit the present invention. Upon review of this specification, certain improvements, modifications, adaptations and variations upon the methods and apparatus disclosed which do not depart from the spirit of the present invention will immediately become apparent. Accordingly, reference should be had to the appended claims in order to ascertain the true scope of the present invention.

For example, the apparatus of the invention might be applied to areas of human anatomy other than the lower back musculature, most obviously to mid-back, upper back or neck areas. Still further, it would be feasible to apply the teachings of the invention to the extremities of the human patient or even to areas of the head. The present invention may also be applied to the analysis of signals from other types of sensors and the techniques described herein used in the diagnosis and treatment of other conditions. While the preferred form of the invention is used in the diagnosis of conditions in human beings, the techniques and apparatus of the invention may also find applicability in diagnostic and treatment activities related to patients which comprise other living organisms.

Thus the method and apparatus of the present invention achieve the above stated objectives, eliminates difficulties encountered in the use of prior devices and systems, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations herein are by way of examples and the invention is not limited to the details shown and described.

In the following claims any feature that is described as a means for performing a function shall be construed as encompassing any means capable of performing the recited function and shall not be limited to the particular means shown in the foregoing description or mere equivalents.

Having described the features, discoveries and principles of the invention, the manner in which it is constructed and operated and the advantages and useful results attained; the new and useful structures, devices, elements, arrangements, parts, combinations, systems, equipment, operations and relationships are set forth in the appended claims.

I claim:

1. Apparatus for collecting surface electromyographic (EMG) signals from a patient, comprising:
   a support member;
   a plurality of electrodes retained in the support member in a predetermined pattern, for positioning on a surface of a patient in a location related to underlying patient anatomy, wherein each of the electrodes includes a patient-contacting electrode head, wherein each electrode head comprises a plurality of discrete patient-contacting pyramid projections for engaging the surface of the patient, and wherein each pyramid projection culminates in a pointed tip for enhancing contact with the surface of the patient;
   the support member being semi-flexible to conform to the external curvature of the patient to allow the electrodes to intimately contact the surface of the patient;
   the support member being sufficiently rigid to maintain the predetermined pattern of the electrodes relative to one another.

2. Apparatus as set forth in claim 1 wherein said predetermined pattern of said electrodes is an array of parallel rows and columns of electrodes.

3. Apparatus as set forth in claim 2 wherein said electrodes are equally spaced in said rows and columns.

4. Apparatus as set forth in claim 1 further comprising a retainer for each electrode, wherein said retainer secures said electrode to said support member for removal from and for positioning said plurality of electrodes on the surface of a patient in said predetermined pattern.

5. Apparatus as set forth in claim 4 wherein each said electrode is of generally bolt-shaped configuration having a patient-contacting head and integral shank and said retainer cooperates with said shank to secure said electrode to said support member.

6. Apparatus as set forth in claim 5 wherein said support member is an elastomeric sheet having a plurality of apertures therein through which said shanks of said electrodes are disposed with said electrode head at one side of said sheet and said retainer at the other side of said sheet.

7. Apparatus as set forth in claim 6 further comprising an electrical connector affixed to said shank of each said electrode and secured by said retainer for transmitting electrical signals from each said electrode to a remote location.

8. Apparatus as set forth in claim 7 further including individual wires routed over the surface of said elastomeric sheet, extending from each said electrode to an electrical connector at one side of said sheet, for removable connection of said apparatus as a unit, from remote electrical apparatus.

9. Apparatus as set forth in claim 5 wherein the pyramid projections are substantially evenly distributed across the electrode head.

10. Apparatus for collecting surface electromyographic (EMG) signals from a patient, comprising:
    a support member;
    a plurality of electrodes retained on the support member in a predetermined pattern, for positioning on a surface of a patient in a location related to underlying patient anatomy, wherein the predetermined pattern of the electrodes is an array of seven columns of electrodes and nine rows of electrodes, wherein the rows and columns of electrodes are generally equally spaced and in parallel;
    the support member being semi-flexible to conform to the external curvature of the patient to allow the electrodes to intimately contact the surface of the patient;
    the support member being sufficiently rigid to generally maintain the predetermined pattern of the electrodes spaced relative to one another.

11. An EMG electrode array for collecting signals from a patient, comprising:
    an elastomeric sheet having a plurality of apertures therein in a configuration of equally spaced columns and rows;
    a generally bolt-shaped electrode positioned in each of the apertures, each electrode having a planar head disposed at one side of the sheet and an integral shaft passing through the aperture, wherein each electrode head comprises a plurality of discrete patient-contacting pyramid projections for engaging a surface of a patient, and wherein each pyramid projection culminates in a pointed tip for enhancing contact with the surface of the patient;

a retainer connected to each of the electrode shafts to secure the electrode to the sheet; and an electrical conductor in connection with each electrode shaft for transmitting electrical signals from the electrode head to a remote location.

12. An electrode array for collecting signals from a patient, comprising:

an elastomeric sheet having a plurality of apertures therein, wherein the apertures in the elastomeric sheet are generally equally spaced in seven columns and nine rows;

a generally bolt-shaped electrode positioned in each of the apertures, each of the electrodes having a planar head disposed at one side of the sheet and an integral shaft passing through the aperture;

a retainer connected to each of the electrode shafts to secure the electrode to the sheet; and an electrical conductor in connection with each of the electrode shafts for transmitting electrical signals from the electrode head to a remote location.

13. An electrode array as set forth in claim 12 wherein each electrode head comprises a plurality of projections, each culminating in a pointed tip for enhancing contact with a surface of a patient.

14. An electrode array as set forth in claim 13 wherein the projections comprise pyramids substantially evenly distributed across the electrode head.

15. An electrode array as set forth in claim 14 wherein said elastomeric sheet is on the order of 0.062 inch thickness, and the altitude of said pyramids is on the order of 0.042 inch.

16. An electrode array as set forth in claim 14 wherein said electrodes in each row and column are spaced 1.162 inch on center and have a head diameter of about 0.375 inch.

17. Apparatus for collecting surface electromyographic (EMG) signals from a patient, comprising:

a support member;

a plurality of electrodes retained in the support member in a predetermined pattern, for positioning on a surface of a patient in a location related to underlying patient anatomy, wherein each of the electrodes includes a patient-contacting electrode head, wherein each electrode head comprises a plurality of discrete patient-contacting projections for engaging the surface of the patient, and wherein each projection has a broad base that tapers to a pointed apex for enhancing contact with the surface of the patient; and the support member being sufficiently flexible to conform to the external curvature of the patient to allow the electrodes to intimately contact the surface of the patient.

* * * * *

UNITED STATES PATENT AND TRADEMARK OFFICE
CERTIFICATE OF CORRECTION

PATENT NO. : 6,002,957
DATED : December 14, 1999
INVENTOR(S) : Mark T. Finneran

It is certified that error appears in the above-identified patent and that said Letters Patent is hereby corrected as shown below:

Title page, title, delete "SUPPORT BELT".

Col. 1, line 1 delete "SUPPORT BELT".

Signed and Sealed this

First Day of August, 2000

*Attest:*

Q. TODD DICKINSON

*Attesting Officer*  *Director of Patents and Trademarks*